(12) United States Patent
Mizoi

(10) Patent No.: US 12,630,062 B2
(45) Date of Patent: *May 19, 2026

(54) CONDITION CORRECTION UNIT

(71) Applicant: TS TECH CO., LTD., Asaka (JP)

(72) Inventor: Kensuke Mizoi, Tochigi (JP)

(73) Assignee: TS TECH CO., LTD., Asaka (JP)

( * ) Notice: Subject to any disclaimer, the term of this patent is extended or adjusted under 35 U.S.C. 154(b) by 40 days.

This patent is subject to a terminal disclaimer.

(21) Appl. No.: 17/222,314

(22) Filed: Apr. 5, 2021

(65) Prior Publication Data

US 2021/0221259 A1 Jul. 22, 2021

Related U.S. Application Data

(63) Continuation of application No. 15/770,014, filed as application No. PCT/JP2016/081250 on Oct. 21, 2016, now Pat. No. 10,967,758.

(30) Foreign Application Priority Data

Oct. 22, 2015 (JP) ................................. 2015-208274

(51) Int. Cl.
B60N 2/56 (2006.01)
A61B 5/00 (2006.01)
(Continued)

(52) U.S. Cl.
CPC .............. B60N 2/56 (2013.01); A61B 5/0816 (2013.01); A61B 5/1126 (2013.01); A61B 5/18 (2013.01);
(Continued)

(58) Field of Classification Search
CPC ... A61B 5/0816; A61B 5/1077; A61B 5/1126; A61B 5/18; A61B 5/4561; A61B 5/6893;
(Continued)

(56) References Cited

U.S. PATENT DOCUMENTS 5,155,685 A * 10/1992 Kishi ....................... B60N 2/66
318/467
5,176,424 A * 1/1993 Tobita .................. B60N 2/7041
297/452.52

(Continued)

FOREIGN PATENT DOCUMENTS

JP H104-071325 U 6/1992
JP H06-081818 U 11/1994
(Continued)

OTHER PUBLICATIONS

Mizoi, Kensuke, WO-2014084283-A1, Jun. 2014, English Translation (Year: 2014).*

(Continued)

*Primary Examiner* — Colin W Stuart
*Assistant Examiner* — Douglas Y Sul
(74) *Attorney, Agent, or Firm* — Michael Best & Friedrich LLP

(57) ABSTRACT

A condition correction unit includes a plan storage unit configured to store correction plans showing contents of correction of the body condition of a seated person, a presentation unit configured to read a correction plan based on a current value measured by a measurement unit from the plan storage unit and present the correction plan to the seated person, and a processing execution unit configured to execute processing to correct posture by controlling an operating unit. The plan storage unit stores the correction plan presented by the presentation unit in association with information identifying the seated person when the correction plan is presented. The processing execution unit reads the correction plan associated with the information identifying the seated person from the plan storage unit, and executes the processing to correct the posture according to correction contents shown by the correction plan.

20 Claims, 14 Drawing Sheets

(51) Int. Cl.

| | |
|---|---|
| *A61B 5/08* | (2006.01) |
| *A61B 5/107* | (2006.01) |
| *A61B 5/11* | (2006.01) |
| *A61B 5/18* | (2006.01) |
| *A61H 1/00* | (2006.01) |
| *A61H 1/02* | (2006.01) |
| *A61H 9/00* | (2006.01) |
| *B60N 2/00* | (2006.01) |
| *B60N 2/02* | (2006.01) |
| *B60N 2/66* | (2006.01) |
| *B60N 2/90* | (2018.01) |

(52) U.S. Cl.

CPC .......... *A61B 5/4561* (2013.01); *A61B 5/6893* (2013.01); *A61B 5/7455* (2013.01); *A61H 1/00* (2013.01); *B60N 2/0023* (2023.08); *B60N 2/0025* (2023.08); *B60N 2/0027* (2023.08); *B60N 2/003* (2023.08); *B60N 2/0228* (2013.01); *B60N 2/0273* (2023.08); *B60N 2/665* (2015.04); *B60N 2/90* (2018.02); *B60N 2/914* (2018.02); *B60N 2/976* (2018.02); *A61B 5/1077* (2013.01); *A61H 1/0292* (2013.01); *A61H 9/0078* (2013.01); *A61H 2201/0149* (2013.01); *A61H 2201/0207* (2013.01); *A61H 2201/1623* (2013.01); *A61H 2201/5002* (2013.01); *A61H 2201/5061* (2013.01); *A61H 2230/625* (2013.01); *B60N 2/026* (2023.08); *B60N 2/0268* (2023.08); *B60N 2002/981* (2018.02); *B60N 2210/24* (2023.08); *B60N 2210/40* (2023.08); *B60N 2220/10* (2023.08)

(58) Field of Classification Search

CPC ...... A61B 5/7455; A61H 1/00; A61H 1/0292; A61H 9/0078; A61H 2201/0149; A61H 2201/0207; A61H 2201/1623; A61H 2201/5002; A61H 2201/5061; A61H 2230/625; B60N 2/002; B60N 2/0228; B60N 2/0244; B60N 2/56; B60N 2/665; B60N 2/90; B60N 2/914; B60N 2/976; B60N 2002/026; B60N 2002/0268; B60N 2002/981

See application file for complete search history.

(56) References Cited

U.S. PATENT DOCUMENTS

| | | | | |
|---|---|---|---|---|
| 6,053,880 A * | 4/2000 | Sleichter, III | ............ | A47C 7/40 |
| | | | | 5/915 |
| 6,438,353 B1 * | 8/2002 | Casey-Cholakis | ....... | G09B 5/06 |
| | | | | 434/350 |
| 6,663,175 B2 * | 12/2003 | Mosquera | ............ | B60N 2/5883 |
| | | | | 219/217 |
| 6,735,798 B1 | 5/2004 | Sekizawa | | |
| 7,334,839 B1 * | 2/2008 | Malerba | ............... | B60N 2/5628 |
| | | | | 297/217.3 |
| 8,410,379 B2 * | 4/2013 | Kuno | ................... | B60N 2/0228 |
| | | | | 200/18 |
| 9,511,646 B2 * | 12/2016 | Müller | ................... | G01N 19/10 |
| 2002/0000742 A1 * | 1/2002 | Wato | ................... | B60R 21/0154 |
| | | | | 297/216.1 |
| 2005/0015258 A1 * | 1/2005 | Somani | ............... | G10H 1/0008 |
| | | | | 704/278 |

| | | | | |
|---|---|---|---|---|
| 2005/0242081 A1 * | 11/2005 | Howick | ............... | B60N 2/5685 |
| | | | | 219/529 |
| 2006/0175877 A1 * | 8/2006 | Alionte | ................ | B60N 2/5685 |
| | | | | 297/180.14 |
| 2008/0319359 A1 * | 12/2008 | Moomiaie-Qajar | ... | A61H 11/00 |
| | | | | 601/152 |
| 2010/0117414 A1 * | 5/2010 | Hwang | ................... | B60N 2/665 |
| | | | | 297/217.3 |
| 2010/0198120 A1 * | 8/2010 | Tago | .................... | A61H 1/0292 |
| | | | | 601/149 |
| 2011/0068611 A1 | 3/2011 | Maeda et al. | | |
| 2011/0275939 A1 * | 11/2011 | Walsh | ................. | G09B 19/003 |
| | | | | 434/257 |
| 2012/0032478 A1 | 2/2012 | Friderich et al. | | |
| 2012/0086249 A1 * | 4/2012 | Hotary | .................... | B60N 2/20 |
| | | | | 297/284.3 |
| 2012/0283855 A1 * | 11/2012 | Hoffman | ............ | A63B 24/0021 |
| | | | | 700/91 |
| 2013/0101975 A1 * | 4/2013 | Hardy | .................... | G09B 19/00 |
| | | | | 434/362 |
| 2013/0233097 A1 * | 9/2013 | Hayner | ................... | A61B 5/11 |
| | | | | 73/865.4 |
| 2014/0167463 A1 * | 6/2014 | Sakata | ................... | B60N 2/914 |
| | | | | 297/284.3 |
| 2015/0178461 A1 | 6/2015 | Kozloski et al. | | |
| 2015/0321590 A1 | 11/2015 | Mizoi et al. | | |
| 2016/0073935 A1 | 3/2016 | van Beest | | |
| 2016/0089059 A1 * | 3/2016 | Hu | ....................... | A61B 5/7207 |
| | | | | 600/595 |
| 2016/0110986 A1 * | 4/2016 | Rosenblood | ......... | A61B 5/4561 |
| | | | | 340/573.7 |
| 2016/0113583 A1 * | 4/2016 | Min | .................... | A47C 31/126 |
| | | | | 600/587 |
| 2016/0339802 A1 | 11/2016 | Hanlon et al. | | |

FOREIGN PATENT DOCUMENTS

| | | | | |
|---|---|---|---|---|
| JP | 2001-152718 A | 6/2001 | | |
| JP | 2001-340163 A | 12/2001 | | |
| JP | 2011-067258 A | 4/2011 | | |
| JP | 2012-517379 A | 8/2012 | | |
| JP | 2014-118030 A | 6/2014 | | |
| JP | 2017-081194 A | 5/2017 | | |
| JP | 2020-001695 A | 1/2020 | | |
| JP | 2021-073129 A | 5/2021 | | |
| WO | WO-2014084283 A1 * | 6/2014 | ............. | B60N 2/002 |

OTHER PUBLICATIONS

Office Action mailed on Dec. 14, 2021, for the related Japanese Patent Application No. 2021-001417, with English machine translation.

Mizoi et al., "English Translation of WO 2014084283," May 6, 2014, 73 pages.

Ogata, "English Translation of JP 1992-071325," May 6, 2001, 6 pages.

Office Action issued in related application JP 2015-208274, Apr. 9, 2019, with machine generated English language translation, 8 pages.

Japanese Office Action mailed on Jul. 25, 2023 from the Japan Patent Office (JPO) for the related Japanese Patent Application No. 2022-120882, with English machine translation.

Japanese Office Action mailed on May 27, 2025 from the Japan Patent Office (JPO) for the related Japanese Patent Application No. 2024-027737, with English machine translation.

* cited by examiner

| CORRECTION PLAN (1) |
| CORRECTION PLAN (2) |
| ⋮ |
| CORRECTION PLAN (n) |

T

| IDENTIFICATION INFORMATION | CORRECTION PLAN |
|---|---|
| aaa | CORRECTION PLAN (1) |
| bbb | CORRECTION PLAN (3) |
| ccc | CORRECTION PLAN (1) |
| ⋮ | ⋮ |
| xxx | CORRECTION PLAN (1) |

FIG. 8

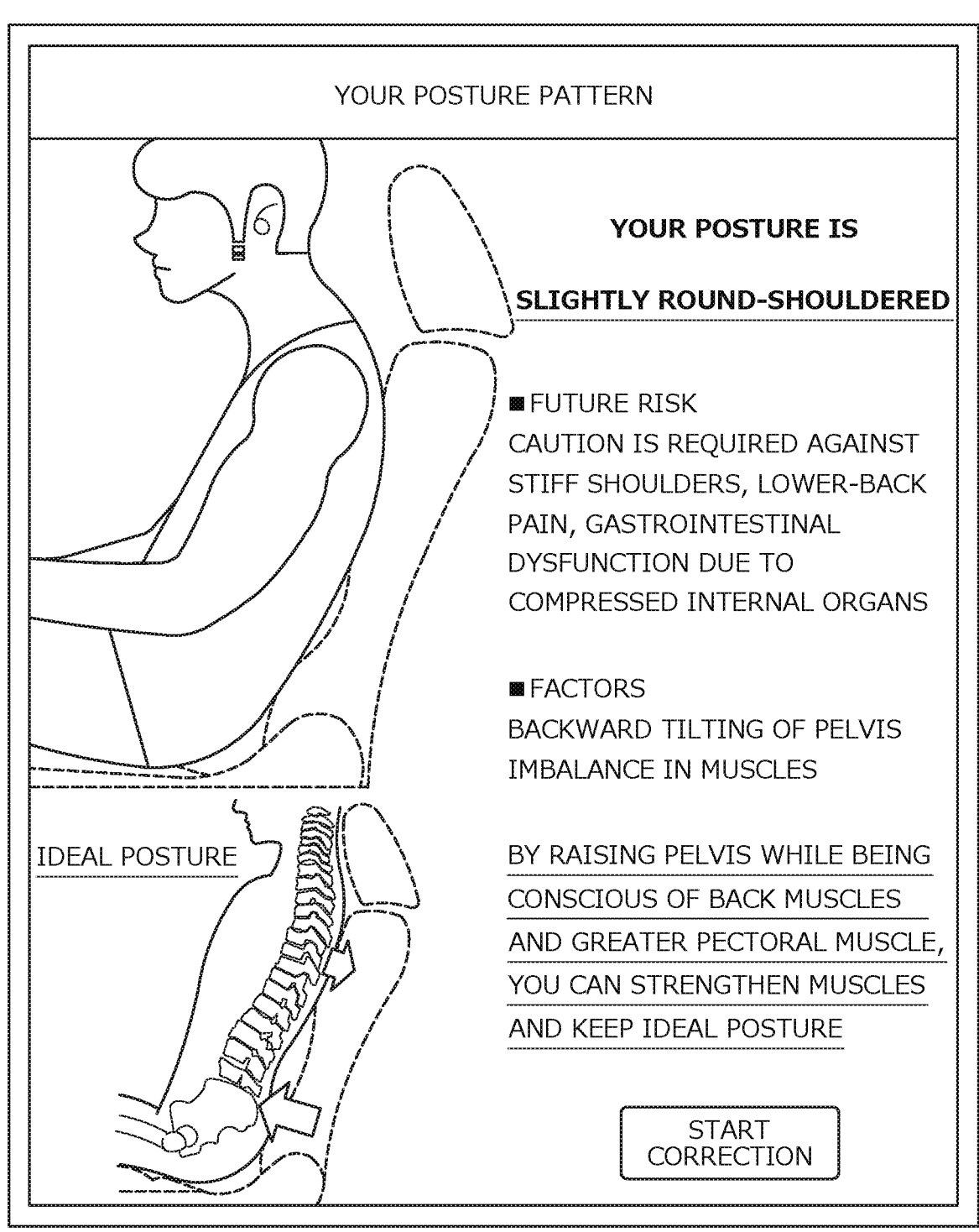

YOUR POSTURE PATTERN

YOUR POSTURE IS

SLIGHTLY ROUND-SHOULDERED

■ FUTURE RISK
CAUTION IS REQUIRED AGAINST
STIFF SHOULDERS, LOWER-BACK
PAIN, GASTROINTESTINAL
DYSFUNCTION DUE TO
COMPRESSED INTERNAL ORGANS

■ FACTORS
BACKWARD TILTING OF PELVIS
IMBALANCE IN MUSCLES

BY RAISING PELVIS WHILE BEING
CONSCIOUS OF BACK MUSCLES
AND GREATER PECTORAL MUSCLE,
YOU CAN STRENGTHEN MUSCLES
AND KEEP IDEAL POSTURE

IDEAL POSTURE

START
CORRECTION

CONDITION CORRECTION UNIT

CROSS-REFERENCE TO RELATED APPLICATIONS

This application is a continuation of U.S. patent application Ser. No. 15/770,014, filed Apr. 20, 2018, now U.S. Pat. No. 10,967,758, which is a National Stage Entry application of PCT Application No. PCT/JP2016/081250, filed Oct. 21, 2016, which claims the priority benefit of Japanese Patent Application No. JP 2015-208274, filed Oct. 22, 2015, the contents being incorporated herein by reference.

BACKGROUND

The present disclosure relates to a condition correction unit that corrects the body condition of a seated person and, more particularly, relates to a condition correction unit capable of correcting the body condition of a seated person with the correction contents suitable for individual characteristics of the seated person.

A technique for correcting the posture or the like of a seated person by detecting the posture or the like of the seated person and moving portions of a seat according to the result of the detection has been already known (see, e.g. Japanese Patent Publication JP 2014-118030 A, "Patent Literature 1"). Specifically, a technique described in Patent Literature 1 detects the posture of a seated person in a vehicle seat and adjusts the bulging pressure of air bags disposed in a backrest of a seatback according to the result of the detection, thereby correcting the posture of the seated person to a proper posture.

In particular, the technique described in Patent Literature 1 uses information provided by a seated posture unique to a seated person as a determination factor for determining the bulging pressure of the air bags (in other words, the shape of the seat). Thus, the shape of a seat, which is less likely to place a burden on a seated person during the correction of posture, can be determined.

Meanwhile, there are individual differences in how the burden is placed. Even if different seated persons are seated in similar postures, the burden placed during the correction can vary among individuals. Thus, for correcting the body condition of a seated person such as his or her seated posture, it is important to grasp in advance individual characteristics of the seated person (such as age and gender) and correct the body condition with the contents suitable for the grasped individual characteristics.

Also, in correcting the body condition of a seated person, typically, a current value of a seated posture or the like is measured to correct the body condition with the contents according to the measurement value. Thus, in terms of setting more proper correction contents, it is preferable to perform a more proper measurement of a body condition.

Further, when correction is performed repeatedly multiple times at different dates and times, it is important for a person to be corrected (that is, a seated person), to manage the effect of each correction (the degree of improvement in the body condition by the correction). This requires a technology (equipment) to inform a seated person of the effect of each correction properly.

SUMMARY

Thus, the present disclosure has been made in view of the above problem, and its object is to provide a condition correction unit capable of correcting the body condition of a seated person with the correction contents suitable for individual characteristics of the seated person. It is another object of the present disclosure to perform a proper measurement of a body condition for correcting the body condition. It is still another object of the present disclosure to inform a seated person of the effect of correction properly.

The above-described problem is solved by a condition correction unit of the present disclosure that includes an operating unit that operates to correct a body condition of a seated person seated in a conveyance seat, an identification information acquisition unit that acquires information identifying the seated person seated in the conveyance seat, a measurement unit that measures a current value of an indicator for determining the body condition, a plan storage unit that stores correction plans showing contents of correction of the body condition, a presentation unit that reads a correction plan based on the current value from the plan storage unit and presents the correction plan to the seated person seated in the conveyance seat, and a processing execution unit that executes processing to correct the body condition by controlling the operating unit, in which the plan storage unit stores the correction plan presented by the presentation unit in association with the information identifying the seated person seated in the conveyance seat when the presentation unit presents the correction plan, and the processing execution unit reads the correction plan associated with the information identifying the seated person seated in the conveyance seat from the plan storage unit, and executes the processing to correct the body condition according to the correction contents shown by the read correction plan.

In the condition correction unit of the present disclosure configured as above, the current value of the indicator for determining body condition is measured, and a correction plan based on the measurement value is presented to a seated person. The presented correction plan is stored in association with information identifying the seated person seated in the conveyance seat when the plan is presented. When correction is performed on the seated person, the correction plan associated with the information identifying the seated person is read and the body condition is corrected according to correction contents shown by the correction plan. As a result, the condition correction unit of the present disclosure can properly correct the body condition of the seated person with the correction contents suitable for individual characteristics of the seated person.

Preferably, the condition correction unit further includes a plan change unit that changes the correction plan associated with the information identifying the seated person seated in the conveyance seat when the presentation unit presents the correction plan, from the correction plan to another of the correction plans stored in the plan storage unit, and the measurement unit re-measures the current value after a date when the processing is started, and in accordance with the current value re-measured by the measurement unit after the date when the processing is started, the plan change unit changes the correction plan associated with the information identifying the seated person seated in the conveyance seat when the presentation unit presents the correction plan. In the above configuration, the body condition is re-measured after the date when correction of the body condition is started. IN accordance with the re-measurement value, the correction plan associated with the information identifying the seated person is changed. This allows a correction plan applied during the correction to be reviewed appropriately as needed, according to the degree of correction (degree of improvement) of the body condition, and more effective correction of the body condition can be made.

More preferably, the condition correction unit further includes a total sitting time management unit that manages a total sitting time that is a cumulative total value of times when a seated person having the same identification information is seated in the conveyance seat, and in accordance with the correction contents shown by the correction plan read from the plan storage unit, the processing execution unit executes the processing to correct the body condition in a correction mode based on the total sitting time. In the above configuration, the body condition is corrected in a correction mode based on a cumulative total value of times when the same seated person is seated in the conveyance seat (total sitting time). This enables proper adjustment of loads during the correction according to the total sitting time. For example, it is possible to perform correction in such a manner that loads are reduced in an early stage of the correction (that is, when the total sitting time is relatively short), and it is possible to perform correction in such a manner that loads are increased gradually as the total sitting time increases.

More preferably, in the condition correction unit, the measurement unit measures the current value on a seated person having the same identification information for a plurality of measurement dates, and the condition correction unit further includes a comparison unit that compares the current value measured by the measurement unit on a previous measurement date with the current value measured by the measurement unit on a measurement date before the previous measurement date. In the above configuration, measurement of body condition on the same seated person is performed for a plurality of measurement dates, and a previous measurement value is compared with a measurement value before the previous measurement value. This comparison enables proper evaluation of the effect of correction (the degree of improvement in body condition by correction).

The condition correction unit may further include a warming unit for warming a predetermined part of the body of the seated person seated in the conveyance seat. The above configuration allows the body of the seated person to be warmed in correction so that the body condition of the seated person is transitioned to an easy-to-correct condition.

The condition correction unit may further include a vibration application unit that applies vibrations to a predetermined part of the body of the seated person seated in the conveyance seat. The above configuration enables application of vibrations to a predetermined body part of a seated person in correction, thereby relaxing tension in the body part (muscle tension) or building up the muscle strength of the body part.

Preferably, the condition correction unit further includes an information display unit that displays information on a screen, and the information display unit displays information based on the current value measured by the measurement unit, and the presentation unit allows the information display unit to display the correction plan on the screen, thereby presenting the correction plan. In the above configuration, the display of a measurement value on body condition and the presentation of a correction plan are performed through a screen. This allows a seated person to check the current body condition, a corresponding correction plan, and additionally the body condition after correction (that is, the effect of correction) through the screen.

Still more preferably, in the condition correction unit, the identification information acquisition unit communicates with a portable terminal held by the seated person seated in the conveyance seat and acquires the identification information from the portable terminal. In the above configuration, information identifying a seated person is acquired through communication with a portable terminal held by the seated person. This configuration enables relatively easy acquisition of information identifying a seated person.

Still more preferably, the condition correction unit further includes a determination unit that determines from the current value a curved condition of a spine as the body condition, and the presentation unit reads a correction plan suitable for the curved condition of the spine determined by the determination unit from the plan storage unit and presents the correction plan to the seated person seated in the conveyance seat. In the above configuration, a curved condition of the spine is determined after measurement on the curved condition of the spine as the body condition is performed. Then, a correction plan according to the determination result is selected and presented to the seated person. This configuration allows a seated person in a so-called round-shouldered posture or backward-bent posture to undergo posture correction suitable for individual characteristics of the seated person.

Still more preferably, in the condition correction unit, the operating unit has a plurality of air bags that are bulged to press the seated person seated in the conveyance seat from a back side, each of the plurality of air bags bulges to a preset bulging pressure in a stage before the seated person is seated in the conveyance seat, the measurement unit uses the bulging pressure, changed due to sitting down in the conveyance seat, as the indicator and measures the current value of the bulging pressure, and the determination unit determines the curved condition of the spine from the current value of the bulging pressure of each of the plurality of air bags. The above configuration corrects the body condition (specifically, the curved condition of the spine) of a seated person using the air bags that press the seated person from the back side. The above configuration measures the current values of the bulging pressures of the air bags, changed due to sitting down in the seat, as measurements on the body condition of the seated person. That is, the above configuration uses the air bags for correction and for measurement of body condition. This enables more effective use of the air bags.

According to the present disclosure, the body condition of a seated person can be properly corrected with correction contents suitable for individual characteristics of the seated person. Further, according to the present disclosure, a correction plan used during the correction can be reviewed appropriately as needed, according to the degree of correction (degree of improvement) of the body condition. Further, according to the present disclosure, loads during the correction can be properly adjusted according to a total sitting time in a conveyance seat. Further, according to the present disclosure, the effect of correction can be evaluated by measuring the body condition of the same seated person for a plurality of measurement dates and comparing measurement values. Further, according to the present disclosure, the body of a seated person can be warmed in correction so that the body condition of the seated person is transitioned to an easy-to-correct condition. Further, according to the present disclosure, vibrations can be applied to a predetermined body part of a seated person in correction to relax tension (muscle tension) in the body part or build up the muscle strength of the body part. Further, according to the present disclosure, a seated person can check the current body condition, a corresponding correction plan, and additionally the body condition after correction through a screen. Further, according to the present disclosure, via communication with a portable terminal held by a seated person, information identifying the seated person can be acquired relatively easily. Further, according to the present disclosure, the curved condition of the spine of a seated person is determined, and therefore the curved condition can be corrected properly with correction contents suitable for individual characteristics of the seated person. Further, according to the present disclosure, the air bags are used for correction and measurement of body condition, and therefore the air bags can be utilized more effectively.

BRIEF DESCRIPTION OF DRAWINGS

FIG. 5 is a diagram showing correction plans and a plan management table stored in a storage unit.

FIG. 8 is a diagram showing an example of a screen when presenting a correction plan.

DETAILED DESCRIPTION

Figure 1:
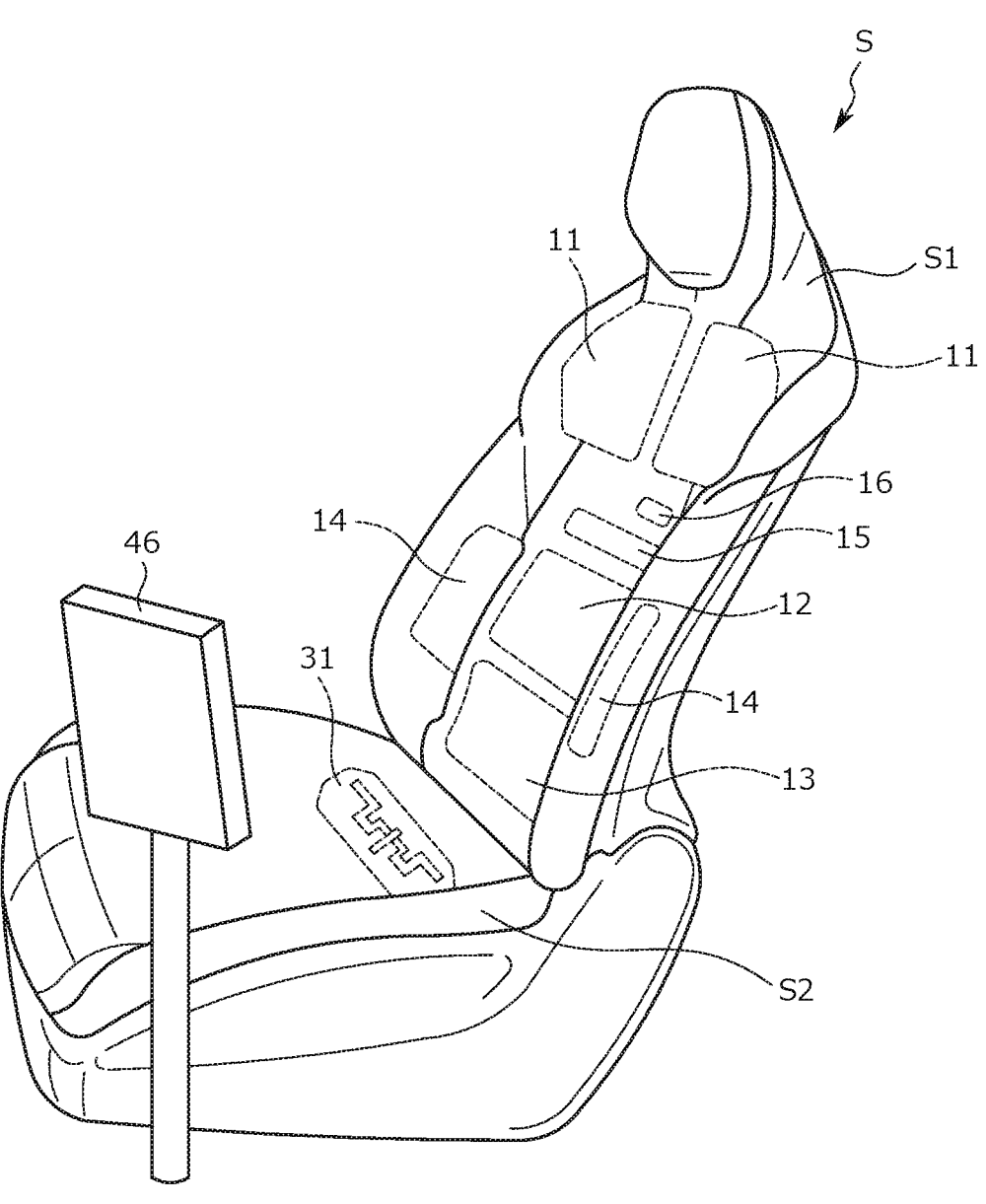
FIG. 1 is a diagram showing an example of a conveyance seat equipped with a condition correction unit of the present disclosure.

Hereinafter, an embodiment of the present disclosure (the present embodiment) will be described using its configuration example and operation example. The following takes a vehicle seat as an example of a conveyance seat, and describes a condition correction unit that corrects the body condition of a seated person seated in a vehicle seat (hereinafter, a seated person). It is noted that the condition correction unit of the present disclosure is also applicable to conveyance seats other than vehicle seats, and specifically, is also applicable to seats mounted on conveyances other than vehicles (such as aircrafts and ships).

In the following description, a "body condition" to be corrected by the condition correction unit of the present disclosure means an orthopedic condition among conditions of a human body, and specifically, is the condition of a skeletal frame, joints, muscles, and others. An example of the body condition may include the curved condition of a spine (in other words, posture), the condition of muscle tension, a distortion in a skeletal frame, or the like. The following describes a configuration for correcting the curved condition of a spine (posture) as the "body condition." However, an object to be corrected by the condition correction unit of the present disclosure is not limited to the curved condition of a spine (posture). Other "body conditions" such as the condition of muscle tension and a distortion in a skeletal frame may be corrected by the condition correction unit of the present disclosure.

<<Overview of Condition Correction Unit According to the Present Embodiment>>

First, an overview of the condition correction unit according to the present embodiment (hereinafter, simply a condition correction unit 1) is described. The condition correction unit 1 is mounted in a vehicle, and is used for the purpose of improving the health condition of a seated person in a vehicle seat S in a stepwise manner. More specifically, the condition correction unit 1 corrects the posture of a seated person, that is, the curved condition of the spine while the seated person is seated in the vehicle seat S. In the present embodiment, posture correction by the condition correction unit 1 is performed continuously, not at one time, and is advanced according to a preset plan (correction plan).

Specifically, for correction plans, a plurality of candidates is prepared, and one correction plan is selected from them. The condition correction unit 1 performs posture correction according to correction contents shown by the selected correction plan. Here, "correction contents" are details of posture correction, examples of which include a part of the body of a seated person on which a load is applied during the posture correction, a load balance between plural body parts when loads are applied to the body parts, a correction duration, a posture as an ultimate goal (specifically, an ideal posture described below), and a standard magnitude of a load during the correction.

In the present embodiment, individual characteristics of a seated person are reflected in the selection of a correction plan. Thus, in the present embodiment, posture correction suitable for individual characteristics of a seated person is performed. This point is a characteristic of the present embodiment, and this characteristic will be described in detail below.

In the present embodiment, the condition correction unit 1 is mounted in a seat corresponding to a driver's seat of vehicle seats S. That is, the condition correction unit 1 is used for correcting the posture of a driver, but not limited thereto. The condition correction unit 1 may be mounted in a seat other than the driver's seat (e.g., a passenger seat or a rear seat).

<<Configuration Example of Condition Correction Unit>>

First, to describe a configuration example of the condition correction unit 1, the configuration of the vehicle seat S in which the condition correction unit 1 is mounted is described. As shown in FIG. 1, the vehicle seat S has a seat back S1 that supports the back of a seated person from behind, a seat cushion S2 that supports the buttocks of a seated person from below, and a headrest S3 that supports the head of a seated person from behind. The basic configuration of each of these seat components is a known configuration and therefore will not be described.

Next, a configuration example of the condition correction unit 1 is described. The condition correction unit 1 includes equipment disposed in or around the vehicle seat S. More specifically, the condition correction unit 1 has equipment, i.e., an operating unit that is installed in the vehicle seat S and operable to correct the posture of a seated person.

To describe the operating unit in detail, there is a plurality of supports including the operating unit in the seat back S1 of the vehicle seat S. Specifically, as shown in FIG. 1, the seat back S1 is provided with a pair of shoulder supports 11, a lumbar support 12, a pelvis support 13, and side supports 14.

The shoulder supports 11 in the seat back S1 are portions that support the shoulders of a seated person in a seated condition on the vehicle seat S (technically, a seated person having standard proportions, and hereinafter, the same applies in this paragraph), and are provided right and left as shown in FIG. 1. The lumbar support 12 in the seat back S1 is a portion that supports the lumbar of a seated person, and is provided in a lower portion of the seat back S1 as shown in FIG. 1. The pelvis support 13 in the seat back S1 is a portion that supports a part of the body of a seated person where the pelvis is located, and is provided below the lumbar support 12 as shown in FIG. 1. The side supports 14 are portions that are laterally fitted to the body of a seated person, and are provided on the inside of portions formed by raised both end portions in the width direction in the seat back S1 (banks) as shown in FIG. 1.

Figure 2:
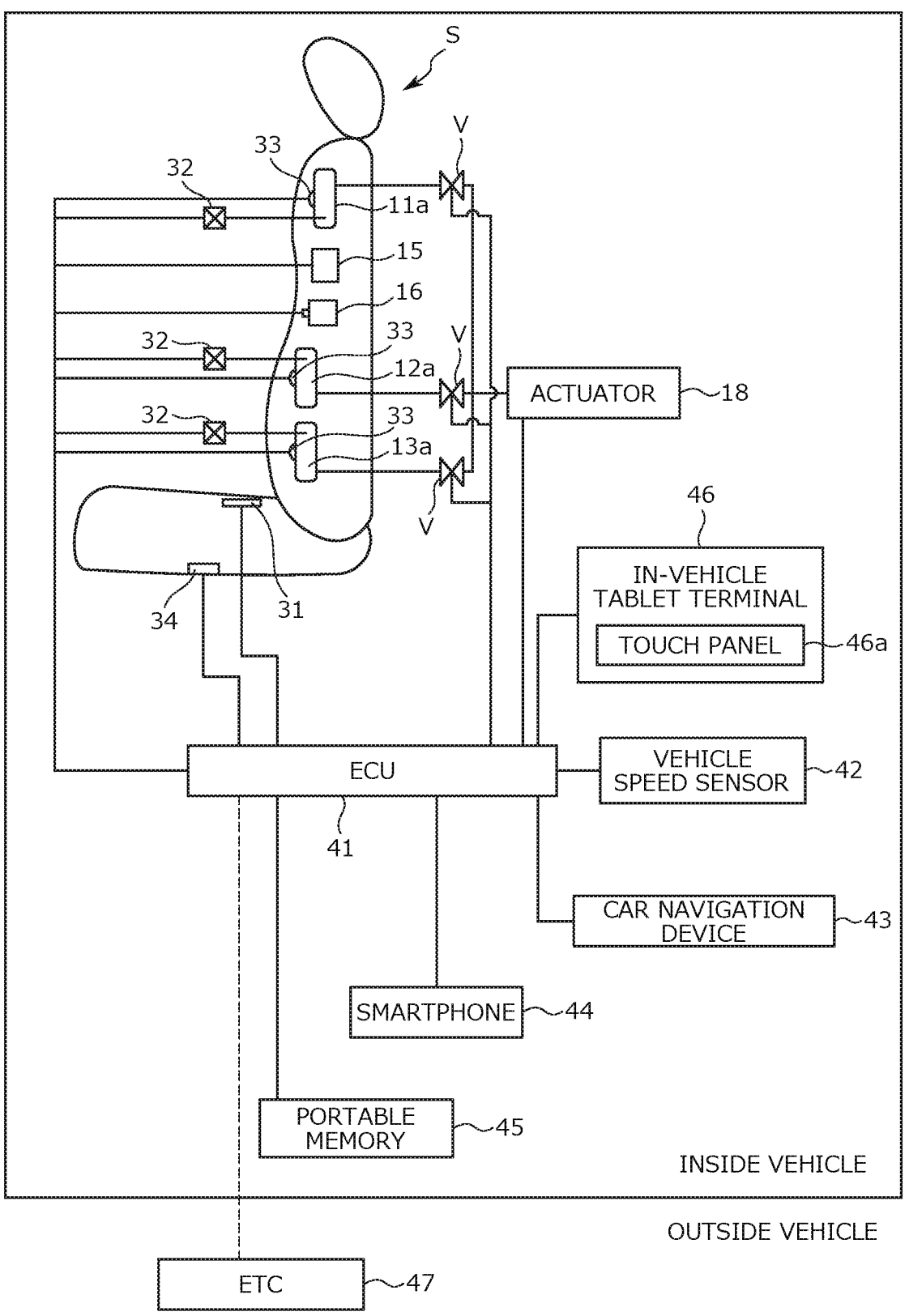
FIG. 2 is a block diagram showing the configuration of the condition correction unit of the present disclosure.

The above-described four supports each have an air bag. Specifically, as shown in FIG. 2, the shoulder supports 11 are each provided with a shoulder air bag 11a, the lumbar support 12 is provided with a lumbar air bag 12a, and the pelvis support 13 is provided with a pelvis air bag 13a. The side supports 14 are also each provided with an air bag, which is not shown in FIG. 2.

The air bags are disposed in the seat back S1 or on the front of the seat back S1. The air bags are filled with air to be bulged. Such bulging of the air bags corrects the posture of a seated person. More specifically, when the air bags are bulged while a seated person is seated in the vehicle seat S, the seated person is pressed from the back side by the air bags. The posture of the seated person is corrected by the pressing forces. Pressing forces produced by the bulging of the air bags correspond to loads acting on a seated person during the posture correction (correction loads).

The supply of air to the air bags is performed by an actuator 18 shown in FIG. 2. The air supplied from the actuator 18 passes through tubes (not shown) that form air supply paths, and is contained into the air bags. Further, in a position at the front of each air bag, an electromagnetic valve V for adjusting the amount of air to be contained into the air bag is installed. The actuator 18 and the electromagnetic valves V described above configure the "operating unit" of the present disclosure together with the air bags.

In the present embodiment, the air bags filled with air to be bulged are used as pressing means that is bulged to press a seated person. Instead, bag bodies bulged by being filled with fluid other than air, e.g. liquid may be used. The present disclosure is not limited to those bulged to press a seated person such as air bags and bag bodies. Members of a fixed shape such as roller-shaped bodies, ball-shaped bodies, or block-shaped bodies may be pressed against a seated person to press the seated person.

Further, in the present embodiment, as shown in FIG. 1, a heater 15 and a vibration application device 16 are provided as auxiliary mechanisms for effectively performing posture correction by the air bags. The heater 15 corresponds to a warming unit, and warms a predetermined part of the body of a seated person seated in the vehicle seat S. The heater 15 is provided and thereby the body of a seated person is warmed from the back side at the time of the posture correction. Warming the body of a seated person from the back side in this manner improves the responsivity (ease of press) of the body of a seated person to the pressing forces (loads) of the air bags, and consequently, further facilitates the posture correction.

The vibration application device 16 corresponds to a vibration application unit, and applies vibrations to a predetermined part of the body (technically, the back) of a seated person seated in the vehicle seat S. The vibration application device 16 is provided and thereby tension (muscle tension) in the back of a seated person is relaxed with the vibrations applied to the back at the time of the posture correction. This improves the responsivity (ease of press) of the body of a seated person to the pressing forces (loads) of the air bags, and consequently, further facilitates the posture correction.

Although the vibration application device 16 is used for relaxing the tension of a seated person in the present embodiment, the use of the vibration application device 16 is not limited to the above content. For example, the vibration application device 16 may be used for the purpose of building up the muscle strength of the back of a seated person. The vibration application device 16 may also be used for the purpose of increasing the wakefulness of a seated person when the wakefulness is low (for example, when the seated person is dozing).

Meanwhile, as shown in FIG. 2, the condition correction unit 1 includes a controller for controlling the above-described operating unit (technically, the actuator 18 and the electromagnetic valves V). The controller includes an electric control unit (ECU) 41 mounted in the vehicle. The ECU 41 has a built-in control circuit for posture correction. When the ECU 41 controls the actuator 18 to be turned on/off and controls the degree of opening of the electromagnetic valves V through the control circuit for posture correction, the bulging pressures of the air bags are adjusted. As a result, pressing forces (loads) corresponding to the bulging pressures of the air bags are applied to the back of a seated person to correct the posture of the seated person.

The ECU 41 communicates with various sensors installed in the vehicle through an in-vehicle network to obtain measurement values of the various sensors. In other words, the ECU 41 can measure the current values of various control items by cooperatively with the various sensors in the vehicle. The control items to be measured by the ECU 41 (that is, objects to be measured) include items relating to the seated condition of a seated person.

More specifically, sensors for measuring the seated condition of a seated person include a respiration sensor 31, bulging pressure sensors 32, pressure sensors 33, and a weight sensor 34. These sensors are used in a state where the sensors are attached to the vehicle seat S.

To describe the sensors, all of the bulging pressure sensors 32 and the pressure sensors 33 are sensors installed to determine the body condition of a seated person, specifically, his or her seated posture. The bulging pressure sensors 32 are installed on the respective air bags to measure the current values of the bulging pressures of the air bags. As in the bulging pressure sensors 32, the pressure sensors 33 are installed on the respective air bags, and specifically are attached to the front of the air bags as shown in FIG. 2 or to the top of the air bags. The ECU 41 measures the current values of indicators for determining the seated posture of a seated person through the bulging pressure sensors 32 and the pressure sensors 33 while the seated person is seated in the vehicle seat S.

More specifically, in the present embodiment, in a stage before a seated person is seated in the vehicle seat S, the air bags (specifically, the shoulder air bags 11a, the lumbar air bag 12a, and the pelvis air bag 13a) are each bulged to a preset bulging pressure. When a seated person sits down in the vehicle seat S in this state, the bulging pressures of the air bags change. The ECU 41 measures the changed bulging pressures of the respective air bags through the bulging pressure sensors 32. Here, the bulging pressures of the air bags (in other words, the bulging pressure balance between the air bags) have values appropriate to the seated posture of the seated person. That is, as an indicator for determining the seated posture of a seated person, the ECU 41 measures the current values of the bulging pressures of the air bags changeable when the seated person sits in the vehicle seat S.

As above, in the present embodiment, the air bags are used both for the posture correction and for the measurement of the seated condition of a seated person. Thus, the air bags are utilized more effectively.

The ECU 41 also measures the current values of pressures applied to the seat back S1 through the pressure sensors 33 provided for the corresponding air bags when a seated person sits in the vehicle seat S. Specifically, when a seated person sits in the vehicle seat S and leans on the seat back S1 and pressures are applied to the front of the air bags from the back of the seated person, the pressure sensors 33 detect the pressures and the ECU 41 measures the magnitudes of the detected pressures through the pressure sensors 33. Here, the pressures measured for the respective airbags vary depending on the installation locations of the air bags. The pressure balance between the air bags has a value appropriate to the seated posture of the seated person. That is, as an indicator for determining the seated posture of a seated person, the ECU 41 measures the current values of pressures when the seated person is seated in the vehicle seat S.

As described above, in the present embodiment, in determining the seated posture of a seated person, two indicators (specifically, the bulging pressures of the air bags and pressures applied to the seat back S1) are measured. This enables more proper determination of a seated posture than when only one of the two indicators is measured. More specifically, when only the bulging pressures of the air bags are measured to determine a seated posture, the bulging pressures changed when a seated person sits in the vehicle seat S are measured. However, even if the bulging pressures are changed, in some cases, it is difficult to determine whether the change is due to sitting down in the seat or due to other reasons (for example, filling of air into the air bags). Meanwhile, when only pressures applied on the seat back S1 are measured by the pressure sensors 33 to determine a seated posture, the measurement by the pressure sensors 33 is not performed correctly unless the back of a seated person is properly in contact with portions of the seat back S1 where the air bags are located.

By contrast, in the present embodiment, two indicators are measured in determining the seated posture of a seated person, and thus the seated posture of a seated person can be determined more properly than in the above-described case where only one indicator is measured, but the present disclosure is not limited to such a configuration. Alternatively, only one of the two indicators may be measured.

The ECU 41 also measures a seated condition other than a seated posture, using the respiration sensor 31 and the weight sensor 34. Specifically, the ECU 41 specifies the wakefulness of a seated person, using the respiration sensor 31 as a pressure-sensitive resistance-type sensor installed in a rear end portion of the seat cushion S2. To describe it more strictly, the ECU 41 measures, with the respiration sensor 31, periodic variations in sitting pressure, which is synchronous with the respiration of a seated (a respiratory waveform), the ECU 4 determines the wakefulness of the seated person from the measurement values. Also, the ECU 41 measures a load acting on the vehicle seat S using the weight sensor 34 and specifies the presence or absence of a seated person from the measurement value.

Further, the ECU 41 communicates with in-vehicle sensors other than the above-described sensors through the in-vehicle network to obtain measurement values of the in-vehicle sensors. For example, the ECU 41 communicates with a vehicle speed sensor 42 to obtain a current value of the travelling speed (vehicle speed).

Furthermore, the ECU 41 can communicate with a communication device other than the above-described ones located in the vehicle through the in-vehicle network to obtain information from the communication device. Specifically, the ECU 41 communicates with a smartphone 44 as a portable terminal held by a seated person to obtain information about the seated person (technically, identification information described below). Further, the ECU 41 communicates with a car navigation device 43 to obtain information about a scheduled distance and a scheduled travelling route to be travelled by the vehicle on that day.

Furthermore, the ECU 41 communicates with an electronic toll collection (ETC) 47 when the vehicle passes in front of the ETC 47, and thereby obtains information for specifying a place where the vehicle is travelling (technically, information indicating whether the vehicle is traveling on an expressway).

Furthermore, the ECU 41 can be connected to a portable memory 45, which is a portable recording medium such as a USB memory or an SD card (registered trademark), and can transfer and receive data to and from the portable memory 45. That is, the ECU 41 can write information stored in it in the portable memory 45 and also can read information stored in the portable memory 45.

Furthermore, the ECU 41 can communicate with a tablet terminal provided in the vehicle (hereinafter, an in-vehicle tablet terminal 46) to display information on a monitor screen (corresponding to a screen) of the in-vehicle tablet terminal 46. More specifically, the in-vehicle tablet terminal 46 is disposed around the vehicle seat S (technically, in a position that allows a seated person to easily operate), and as shown in FIG. 1, the in-vehicle tablet terminal 46 is set on the top of a stanchion extending upward from the floor of the vehicle body.

The ECU 41 generates data for displaying image information and character string information (information display data) and transmits the information display data to the in-vehicle tablet terminal 46. The in-vehicle tablet terminal 46 receives the information display data through the in-vehicle network and then develops this, and displays the information indicated by the data on the monitor screen. This allows the seated person to check various kinds of information transmitted from the ECU 41 on the monitor screen, and as shown in FIG. 3, for example, the seated person can check the seated condition measured by the ECU 41.

Figure 3:
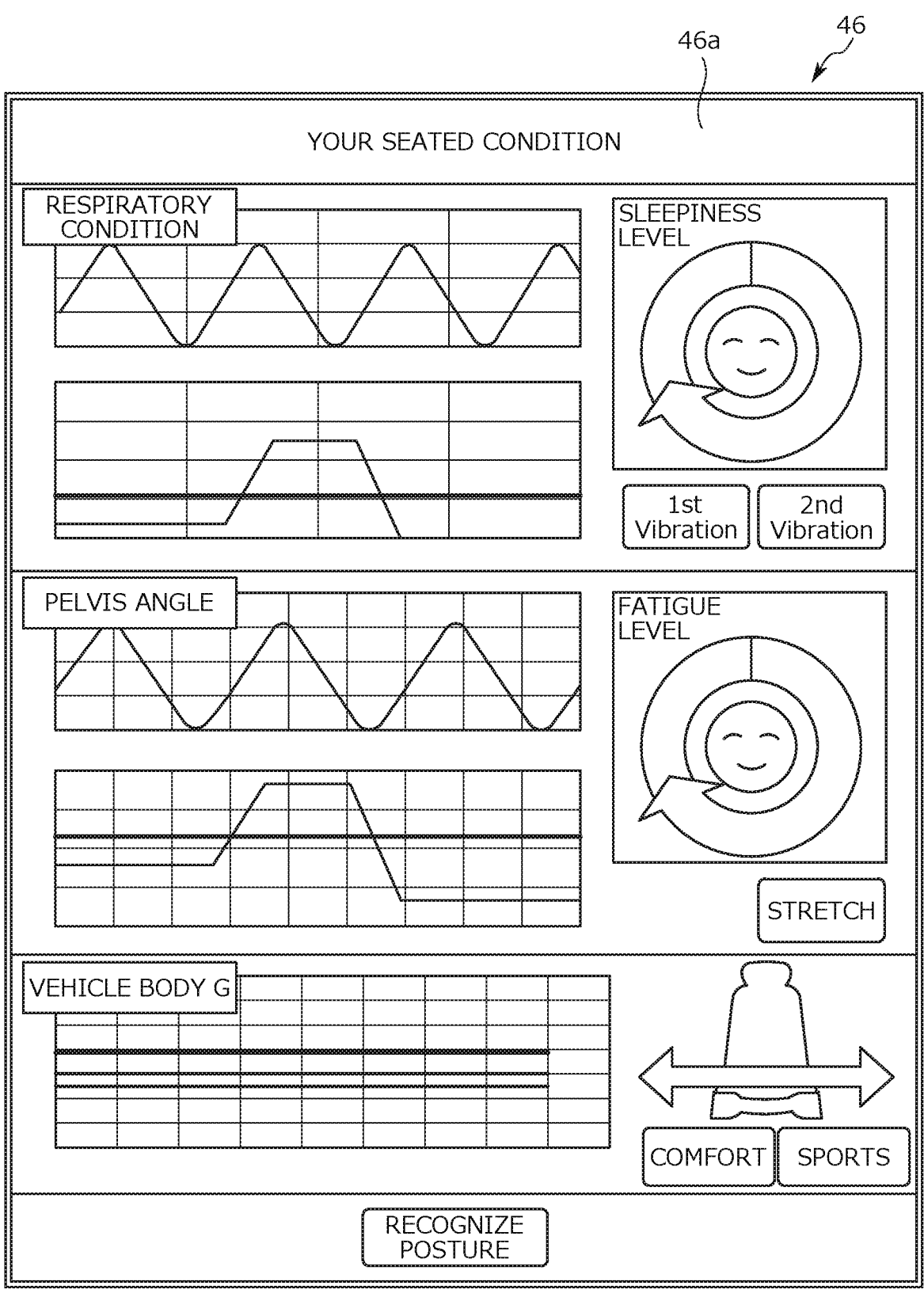
FIG. 3 is a diagram showing a screen for checking the body condition of a seated person.

A screen example shown in FIG. 3 is only an example of the monitor screen. The design and screen layout thereof are not limited to those shown in FIG. 3 and can be set as desired. Further, in FIG. 3, information on the respiratory condition (technically, a respiratory waveform and a wakefulness determination graph), information on the angle of the pelvis (technically, a change curve of the pelvis angle and a fatigue level determination graph), and the inclination of the vehicle body (indicated as vehicle body G in the figure) are displayed as the seated condition. Information displayed on the monitor screen is not limited to the above contents.

The monitor screen of the in-vehicle tablet terminal 46 includes a touch panel 46a, and the monitor screen displays information indicated by information display data and receives a screen operation (touch operation) performed by a seated person as an input operation.

<<About Functions of Controller>>

Figure 4:
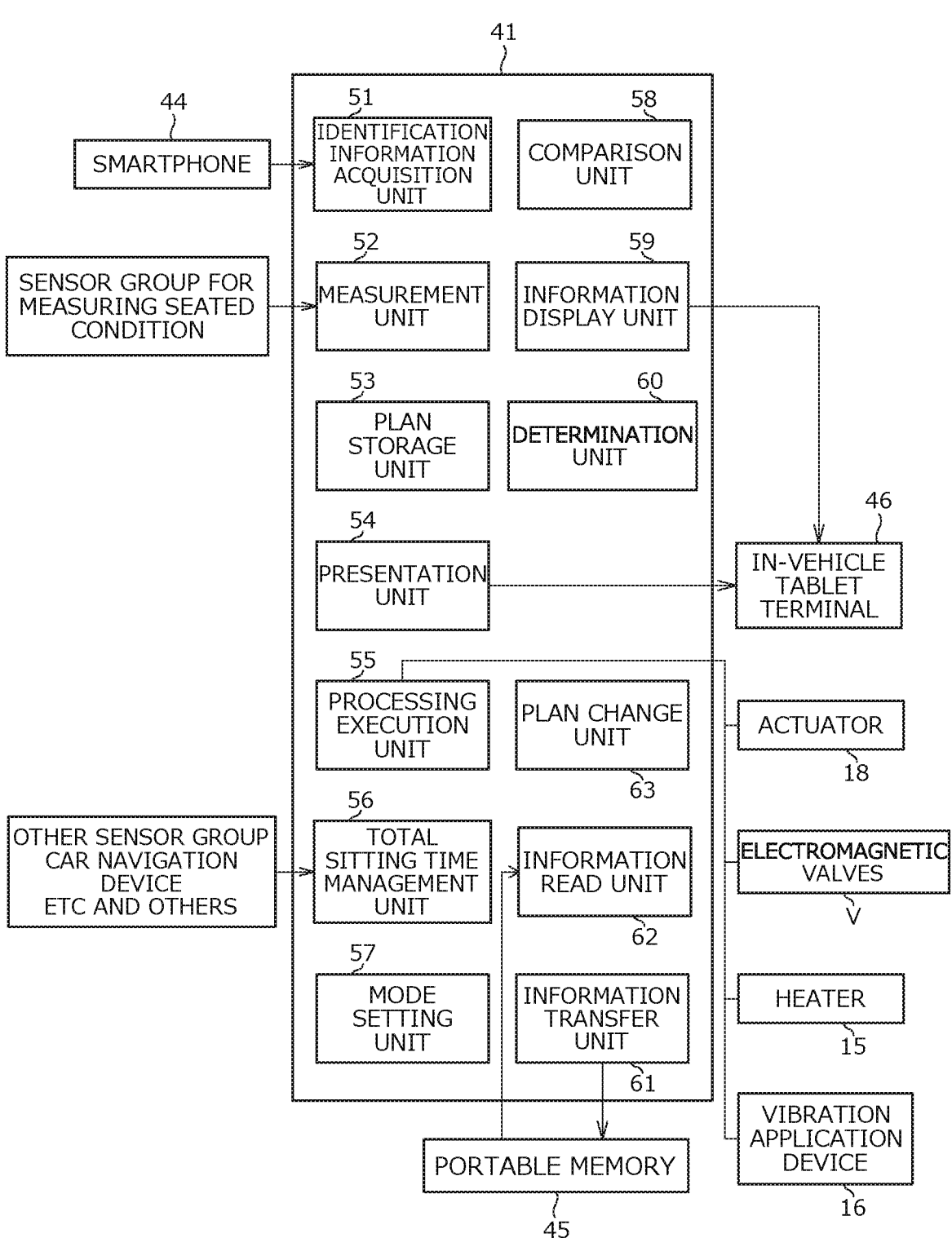
FIG. 4 is a diagram showing the configuration of an ECU as a controller from a functional standpoint.

Next, with reference to FIG. 4, functions of the ECU 41 as a controller will be described. The ECU 41 includes various functions relating to the posture correction. Specifically, as shown in FIG. 4, the ECU 41 has an identification information acquisition unit 51, a measurement unit 52, a plan storage unit 53, a presentation unit 54, a processing execution unit 55, a total sitting time management unit 56, a mode setting unit 57, a comparison unit 58, an information display unit 59, a determination unit 60, an information transfer unit 61, an information read unit 62, and a plan change unit 63. These functional units are each implemented by hardware constituting the ECU 41 (specifically, a microprocessor unit (MPU) and a memory) cooperatively with software to provide a control circuit for posture correction.

Hereinafter, each of the above functional units is described. It is noted that the order of the following descriptions of the functional units is different from the above listing order of the functional units.

(Identification Information Acquisition Unit 51)

The identification information acquisition unit 51 acquires information identifying a seated person. Here, identification information is information for identifying a seated person (personal verification), and for example, corresponds to ID information of the seated person, image information indicating a face image or a fingerprint image of the seated person, voice print information of the seated person, or the like.

In the present embodiment, the identification information acquisition unit 51 communicates with a smartphone 44 held by a seated person to obtain identification information from the smartphone 44. With this configuration, when a person holding a smartphone 44 sits down in the vehicle seat S, the ECU 41 communicates with the smartphone 44, thereby automatically obtaining information identifying the seated person. As a result, in the present embodiment, information identifying a seated person can be obtained relatively easily.

It is noted that a way of acquiring identification information is not limited to the above-described way. Identification information may be acquired in such a manner that a seated person enters identification information through the in-vehicle tablet terminal 46 or a predetermined input device, and the ECU 41 receives data on the identification information (contents of the input operation) from the device that has received the input operation. Alternatively, identification information may be acquired by taking a face image of a seated person with a camera installed in the vehicle or by recording the voice of a seated person by a microphone installed in the vehicle. Alternatively, a sensor for identifying a seated person may be installed in the vehicle (near a handle, for example) so that the ECU 41 acquires identification information (a result of detection by the sensor) from the sensor.

(Measurement Unit 52)

The measurement unit 52 measures the body condition of a seated person seated in the vehicle seat S, that is, the seated condition, using a sensor group provided in the vehicle for measuring the seated condition. Specifically, using the bulging pressure sensors 32 provided for the respective air bags, the measurement unit 52 measures the current values of the bulging pressures of the air bags that have changed when a seated person sits down in the vehicle seat S. The measurement unit 52 also measures the current values of pressures applied on portions of the seat back S1 when the seated person is seated in the vehicle seat S, using the pressure sensors 33 attached to the front of the air bags. The measurement unit 52 also measures the respiratory waveform of the seated person, using the respiration sensor 31. The measurement unit 52 also measures a load acting on the vehicle seat S, using the weight sensor 34.

It is noted that objects to be measured by the measurement unit 52 and a method of measurement by the measurement unit 52 are not limited to the above details. It is only necessary to measure an indicator for specifying the body condition of a seated person by a suitable method. For example, the skeletal frame shape of a seated person may be measured with a known shape sensor. Alternatively, by taking an image of a seated person with an in-vehicle camera and analyzing the taken image, the curved condition of the spine of the seated person, a distortion in the skeletal frame, or the like may be measured.

As described above, the measurement unit 52 measures the seated condition of a seated person (specifically, the current values of the bulging pressures of the air bags and pressures applied to the seat back S1). In the present embodiment, the measurement unit 52 performs measurement on the same seated person (that is, a seated person having the same identification information) for plural measurement dates. More specifically, when a person uses the vehicle over a period of multiple days, the measurement unit 52 measures the seated condition of the person on a daily basis.

Values of day-to-day measurement by the measurement unit 52 are stored as a measurement history. The measurement history is associated with information identifying a seated person, and is managed for each seated person.

(Determination Unit 60)

The determination unit 60 determines a seated posture (the curved condition of a spine) from the current values of indicators for determining a seated posture (specifically, bulging pressures measured by the bulging pressure sensors 32 and pressures measured by the pressure sensors 33) among current values relating to a seated condition measured by the measurement unit 52. More specifically, the determination unit 60 selects the corresponding one of five postures, "round-shouldered," "slightly round-shouldered," "ideal posture," "slightly backward-bent," and "backward-bent" and sets the selection result as the current seated posture of a seated person.

It can be set as desired in what range the current values of the indicators measured by the measurement unit 52 (i.e., measurement values) are when they correspond to one of the five seated postures. Seated posture candidates are not limited to the above five postures and can be determined as desired.

(Plan Storage Unit 53)

The plan storage unit 53 stores correction plans to be applied during the posture correction. In the present embodiment, a plurality of correction plans has been prepared in advance. The plan storage unit 53 stores n pieces of (n is a natural number equal to or larger than 2) correction plans as shown in FIG. 5.

Also, the plan storage unit 53 stores a plan management table T shown in FIG. 5 together with the correction plans.

The plan management table T is data for managing correction plans set for seated persons. More specifically, the plan management table T defines the correspondence relationship between information identifying a seated person acquired by the identification information acquisition unit 51 and a correction plan applied when posture correction is performed on the seated person identified by the identification information. For example, when posture correction is performed on a seated person of identification information "aaa," a correction plan (1) is applied.

(Presentation Unit 54)

The presentation unit 54 reads a correction plan suitable for a seated posture determined by the determination unit 60 from the plan storage unit 53 and presents the correction plan to a seated person. Here, when the determination unit 60 determines a seated posture, the seated posture is determined based on current values relating to a seated condition measured by the measurement unit 52 as described above. In this context, the presentation unit 54 presents the correction plan based on current values relating to a seated condition measured by the measurement unit 52.

To describe in detail the presentation of a correction plan by the presentation unit 54, the presentation unit 54 refers to a table for defining the correspondence relationships between seated postures and correction plans (hereinafter, a correspondence table), selects one of the correction plans, which is associated with the seated posture of a seated person determined by the determination unit 60, and presents the correction plan. In the correspondence table, different correction plans suitable for different seated postures are defined. When a seated posture is determined, one of the corresponding correction plans is selected based on the correspondence table.

The correction plan presented to a seated person is stored in the plan storage unit 53 in association with information identifying the seated person. That is, the plan storage unit 53 stores the correction plan presented by the presentation unit 54 in association with information identifying a seated person seated in the vehicle seat when the presentation unit 54 presents the correction plan. More specifically, when the presentation unit 54 presents the correction plan, a new record is added to the plan management table T stored by the plan storage unit 53. This record is data for associating the correction plan presented by the presentation unit 54 this time with the information identifying the seated person when the plan is presented.

(Processing Execution Unit 55)

The processing execution unit 55 executes processing to correct a seated posture (hereinafter, correction processing). In correction processing, the processing execution unit 55 controls the actuator 18 and the electromagnetic valves V to adjust the bulging pressures of the air bags. Therefore, the back of a seated person t is pressed by the air bags. As a result, the seated posture of the seated person is corrected.

In the present embodiment, for posture correction, the processing execution unit 55 specifies information identifying a seated person seated in the vehicle seat S at the time and reads a correction plan associated with the identified identification information from the plan storage unit 53. Then, the processing execution unit 55 executes correction processing according to correction contents shown by the read correction plan. Thus, in the present embodiment, in correcting the seated posture of a seated person, the correction is performed with the contents shown by the correction plan presented to the seated person. As a result, the seated posture of the seated person is corrected properly with the correction contents suitable for the seated posture of the seated person.

Figures 6A, 6B, 6C:
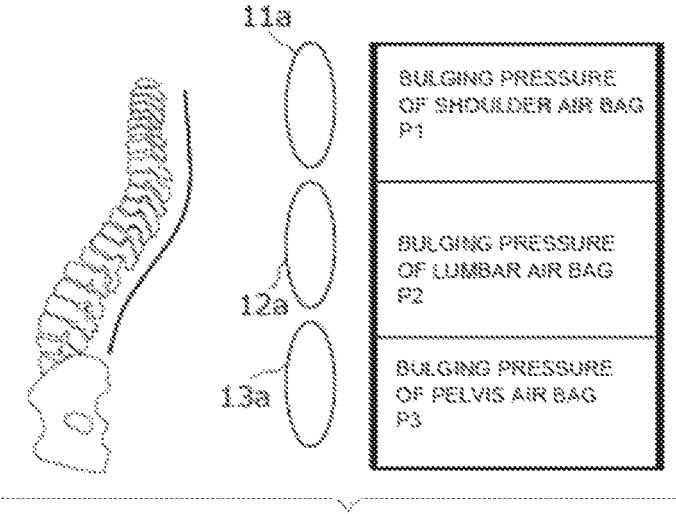
FIG. 6A is an explanatory diagram of a correction method for correcting a round-shouldered posture.
FIG. 6B is a diagram showing a condition in an ideal posture.
FIG. 6C is an explanatory diagram of a correction method for correcting a backward-bent posture.

Specifically, in correction processing, the processing execution unit 55 adjusts the bulging pressures of the shoulder air bags 11*a*, the lumbar air bag 12*a*, and the pelvis air bag 13*a*, according to the seated posture of a seated person (that is, a determination result by the determination unit 60). For example, when the seated posture is round-shouldered, as shown in FIG. 6A, the bulging pressures of the shoulder air bags 11*a*, the lumbar air bag 12*a*, and the pelvis air bag 13*a* are made larger in the mentioned order so that the bulging pressure of the pelvis air bag 13*a* (indicated with P3 in the figure) is largest. FIG. 6A and FIGS. 6B and 6C described below are diagrams showing the positional relationships between the spine and the air bags in different seated postures and are schematic diagrams showing the magnitude relationships in bulging pressure between the air bags.

Contrarily, when the seated posture is backward-bent, as shown in FIG. 6C, the bulging pressure of the shoulder air bags 11*a* (indicated with P1 in the figure) is set largest, and the bulging pressure of the lumbar air bag 12*a* (indicated with P2 in the figure) is set smallest. Meanwhile, when the seated posture is the ideal posture, as shown in FIG. 6B, the bulging pressure of the lumbar air bag 12*a* is set larger than the bulging pressure of the shoulder air bags 11*a*, and the bulging pressure of the pelvis air bag 13*a* is set slightly larger than the bulging pressure of the lumbar air bag 12*a*. It is noted that the correction contents shown in FIGS. 6A to 6C (specifically, the balance in bulging pressure between the air bags) are only an example are not limited to the contents shown in these figures.

In the present embodiment, the processing execution unit 55 corrects the seated posture of a seated person in a correction mode set by the mode setting unit 57 described below when executing correction processing. Here, a "correction mode" is a specific procedure (correction process) of posture correction or a correction mode. For example, the degree of loads applied to the body of a seated person during the posture correction (technically, the rate of change of loads, a load application schedule, the magnitudes of loads in each time period, and the like) correspond to a correction mode. In the present embodiment, a correction mode is set every time correction processing is executed according to the condition and schedule of a seated person on that day, the conditions of the vehicle and the surroundings, and other matters to be considered in setting a correction mode.

Further, for execution of correction processing, the processing execution unit 55 controls the heater 15 to warm the back of a seated person (specifically, a part of the back located immediately located in front of the heater 15). Furthermore, for execution of correction processing, the processing execution unit 55 controls the vibration application device 16 to apply vibrations to the back of the seated person. Thus, muscles of the seated person (especially muscles of the shoulders, back, and waist) are relaxed: thereafter, the subsequent posture correction is performed efficiently.

(Total Sitting Time Management Unit 56)

The total sitting time management unit 56 manages a total sitting time for each seated person. Here, a "total sitting time" means a cumulative total value of times when a seated person having the same identification information is seated in the vehicle seat S. In the present embodiment, a total sitting time is managed relative to the starting time of posture correction when a seated person undergoes posture correction for the first time (starting point). That is, in the present embodiment, a total sitting time is synonymous with a cumulative total time for which a seated person has undergone posture correction.

The total sitting time management unit 56 stores a total sitting time of a seated person in association with information identifying the seated person, and specifically, stores a management table defining the correspondence relationship between a total sitting time and identification information (hereinafter, a total sitting time management table).

To describe the management of a total sitting time in detail, when a seated person sits down in the vehicle seat S, the total sitting time management unit 56 specifies the total sitting time of the seated person up to the last time, based on identification information acquired by the identification information acquisition unit 51 at the time and the above-described total sitting time management table. Meanwhile, the total sitting time management unit 56 counts sitting time from the point in time when the seated person sits down in the vehicle seat S, and combines the determined total sitting time up to the last time and the new sitting time being counted, thereby determining the present total sitting time. Then, the total sitting time management unit 56 updates, in the total sitting time management table, the total sitting time associated with the information identifying the seated person seated in the vehicle seat S to the total sitting time determined this time.

(Mode Setting Unit 57)

The mode setting unit 57 sets a correction mode to be applied when the processing execution unit 55 executes correction processing. In the present embodiment, as described above, the mode setting unit 57 sets a correction mode each time correction processing is executed. In the present embodiment, the mode setting unit 57 sets a correction mode based on various conditions. Specifically, a correction mode corresponding to each of the following matters (r1), (r2), (r3), (r4), (r5), and (r6) is set. (r1) a total sitting time associated with information identifying a seated person seated in the vehicle seat S among total sitting times managed by the total sitting time management unit 56

(r2) the age of the seated person seated in the vehicle seat S (r3) a scheduled travelling route to be traveled by the vehicle on that day (r4) the day of the week of that day and the current time (r5) a place where the vehicle is travelling (whether the vehicle is traveling on an expressway)

(r6) the travelling speed of the vehicle

As above, in the present embodiment, the above six matters are considered to set a correction mode, so that posture correction is performed in a proper mode after the degree of progress of posture correction (that is, a time for which a seated person has undergone posture correction), a schedule of the seated person, and others have been taken into consideration. Specifically, a seated person undergoes posture correction in a correction mode based on a total sitting time till then. Thus, loads during the correction are adjusted properly according to a total sitting time. For example, loads can be reduced in an early stage of the correction (that is, when the total sitting time is relatively short), and loads can be gradually increased as the total sitting time increases.

When the vehicle travels for a relatively long distance, a seated person is seated in the vehicle seat S for a long time. Thus, a correction mode can be set to make the duration of posture correction longer than a normal time. When the vehicle is driven on a particular day of the week (e.g. on a holiday) or at a particular time (e.g. in the early morning), posture correction can be performed in a correction mode suitable for that day of the week or the time period. During a period when the vehicle is traveling on an expressway, the seated posture of a seated person is stabilized, and thus a correction mode can be set to more frequently apply loads to the seated person.

Of the above six matters, (r1), (r4), (r5), and (r6) dynamically change during a period when the vehicle is travelling. During a vehicle travelling period, the mode setting unit 57 periodically specifies these four matters, and updates the correction mode as appropriate according to the determination results. Thus, in the present embodiment, the correction mode is periodically updated during execution of correction processing. When the correction mode is changed, the processing execution unit 55 executes correction processing in the changed correction mode.

In the present embodiment, of the above six matters, information about (r2) is obtained via input by a seated person through the in-vehicle tablet terminal 46 or a predetermined input device, but not limited thereto. The age of a seated person can be obtained via analyzation of a face image of the seated person taken by a camera installed in the vehicle or via measurement of a piece of information with a predetermined sensor, which varies with the age (such as the number of wrinkles, bone density, or a body fat percentage) among pieces of biological information on the seated person. The age may be an actual age (real age) or may be an age that depends on physical strength or health condition (so-called physical age).

In the present embodiment, information about (r3) is obtained via communication of the ECU 41 with the car navigation device 43, but not limited thereto. A scheduled travelling route of the vehicle can be obtained via input by a seated person through the in-vehicle tablet terminal 46 or a predetermined input device.

In the present embodiment, information about (r4) is obtained from a calendar or an internal clock in the ECU 41, but not limited thereto. The day of the week of that day and the current time can be obtained via communication of the ECU 41 with an external apparatus or a smartphone 44 of a seated person.

In the present embodiment, information about (r5), specifically, information on whether the vehicle is currently travelling on an expressway is obtained when the ECU 41 receives an output signal from an ETC 47 while the vehicle is passing in front of the ETC 47, but not limited thereto. Whether the vehicle is currently travelling on an expressway can be obtained with GPS mounted in the vehicle, a smartphone 44, or the in-vehicle tablet terminal 46. Alternatively, whether the vehicle is currently travelling on an expressway can be obtained via input by a seated person through the in-vehicle tablet terminal 46 or a predetermined input device.

In the present embodiment, information about (r6) is obtained when the ECU 41 receives an output signal from the vehicle speed sensor 42, but not limited thereto. The vehicle travelling speed can be obtained via input by a seated person through the in-vehicle tablet terminal 46 or a predetermined input device.

In the present embodiment, a correction mode is set according to the above six matters (r1) to (r6). Matters to be considered in setting a correction mode are not limited to the above six matters. Only one or some of the above six matters may be considered. Alternatively, a matter other than the above six matters (such as the physical condition of a seated person or the conditions of a road surface on which the vehicle is travelling) may be further considered to set a correction mode.

(Information Display Unit 59)

The information display unit 59 displays information on the touch panel 46a of the in-vehicle tablet terminal 46. More specifically, the information display unit 59 generates data for displaying information (information display data) and transmits it to the in-vehicle tablet terminal 46. The in-vehicle tablet terminal 46 receives the information display data through the in-vehicle network, and then develops this and displays the information indicated by the data on the monitor screen.

To describe information display data transmitted by the information display unit 59, data for displaying a result of determination by the determination unit 60 is transmitted as information display data. That is, in the present embodiment, the information display unit 59 displays information showing a determination result of the determination unit 60, specifically, the current seated posture of a seated person. Here, as described above, the determination unit 60 determines a seated posture, based on current values relating to a seated condition measured by the measurement unit 52. In this context, the information display unit 59 displays information based on current values relating to a seated condition measured by the measurement unit 52.

Figure 7:
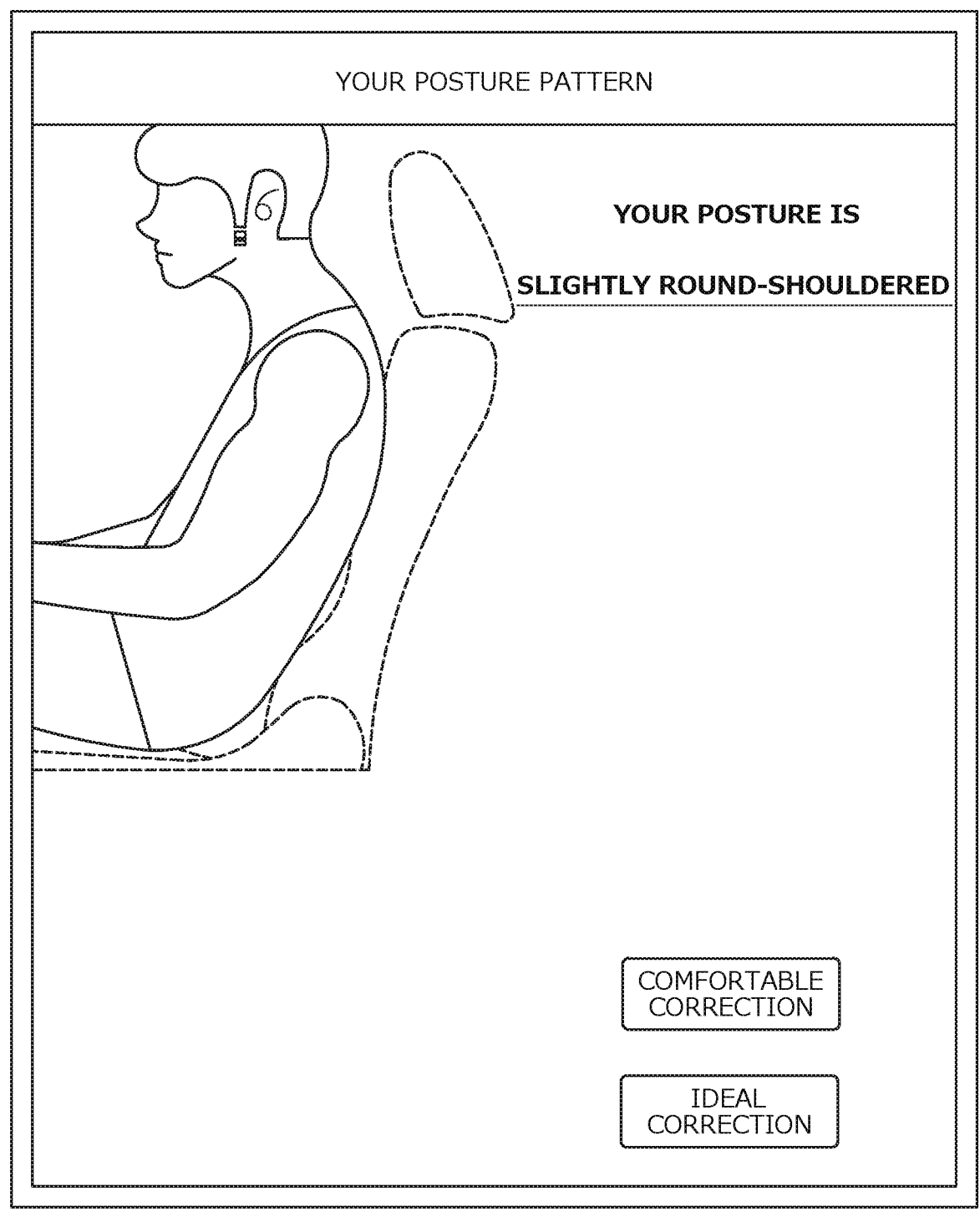
FIG. 7 is a diagram showing an example of a screen when showing the result of posture determination.

FIG. 7 shows a screen example on which a result of determination by the determination unit 60 is displayed. It is noted that the screen shown in FIG. 7 is an example of a screen on which a result of determination by the determination unit 60 is displayed. Screen design, screen layout, and information displayed are not limited to the contents shown in FIG. 7.

Information display data transmitted by the information display unit 59 includes data for displaying a correction plan presented by the presentation unit 54. That is, in the present embodiment, the presentation unit 54 presents a correction plan by allowing the information display unit 59 to display the correction plan on the screen of the in-vehicle tablet terminal 46.

FIG. 8 shows a screen example on which a correction plan presented by the presentation unit 54 is displayed. Here, in the screen, the correction plan includes future risk and factors associated with a current seated posture, an ideal posture, and correction contents (a portion written as "By raising pelvis . . . keep ideal posture." in the figure). However, display contents when a correction plan is displayed on the screen are not limited to the contents shown in FIG. 8. Screen design and screen layout for displaying a correction plan presented by the presentation unit 54 are not limited to the contents shown in FIG. 8.

In the present embodiment, the information display unit 59 displays information on the touch panel 46a of the in-vehicle tablet terminal 46, but not limited thereto. For example, the information display unit 59 may display information on a smartphone 44 held by a seated person or another screen mounted in the vehicle (e.g. a display of the car navigation device 43).

(Comparison Unit 58)

The comparison unit 58 compares a seated condition measured by the measurement unit 52 at the time of the previous measurement on the same seated person (specifically, measurement values of the bulging pressures of the air bags and pressures applied to the seat back S1) with a seated condition measured at the time of measurement before the time of the previous measurement. Specifically, when a seated person sits down in the vehicle seat S, measurement of the seated condition by the measurement unit 52 (that is, present measurement) is performed. Meanwhile, the comparison unit 58 refers to the measurement history of the seated person and reads measurement values of the seated condition in the first measurement (first measurement values).

Then, the comparison unit 58 compares the present measurement values with the first measurement values. This comparison enables grasping of the effect of posture correction that has been performed until the last time (that is, the degree of posture improvement by the correction).

Figure 9:
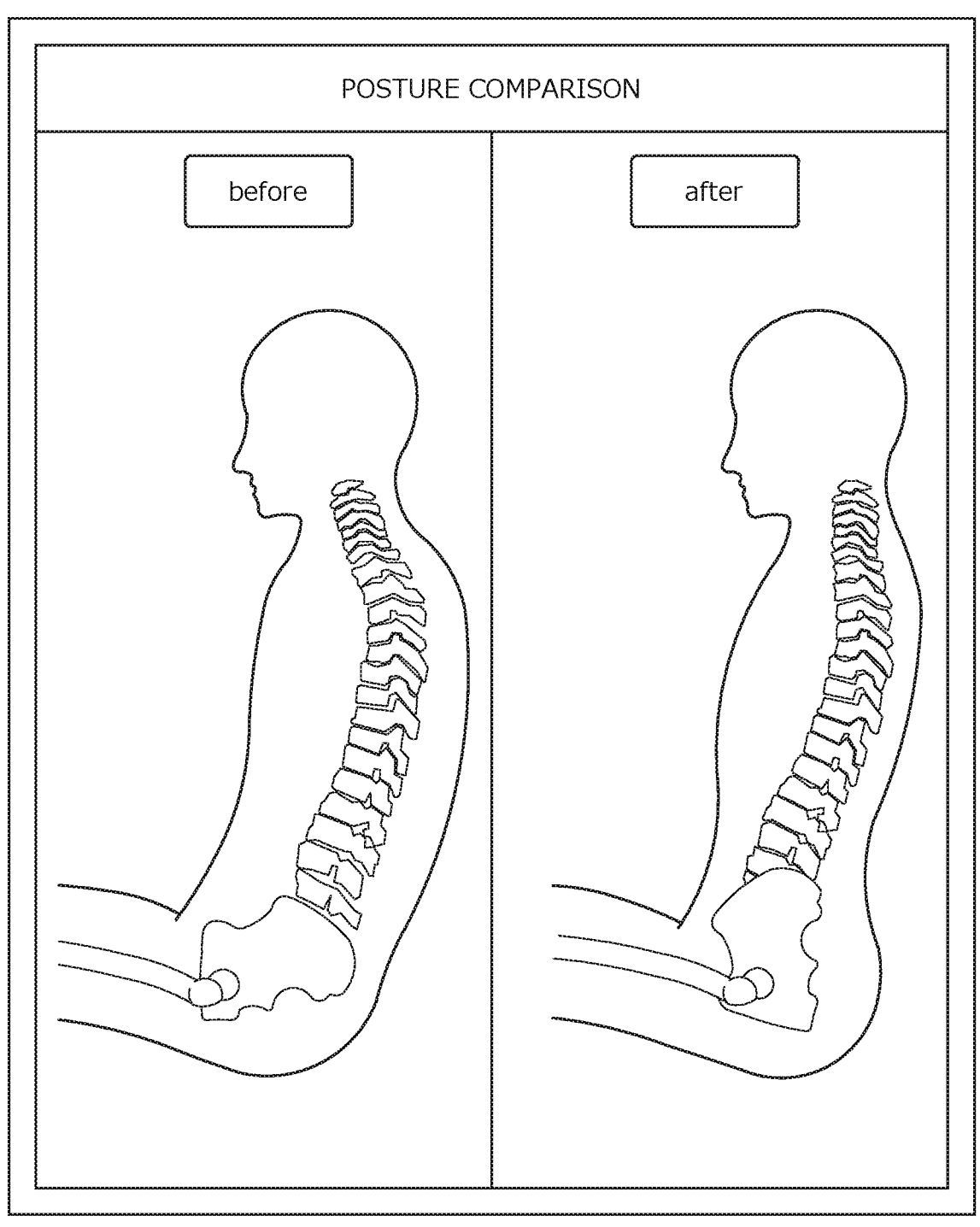
FIG. 9 is a diagram showing an example of a screen when showing the results of posture comparison.

In the present embodiment, as shown in FIG. 9, about the present measurement values and the first measurement values compared, the information display unit 59 displays separate pieces of information based on the measurement values (technically, images each showing the curved condition of the spine corresponding to the measurement values) on the in-vehicle tablet terminal 46. This allows the seated person to check the effect of posture correction that has been performed until the last time (that is, the effect of posture improvement by the correction) through the in-vehicle tablet terminal 46.

A screen shown in FIG. 9 is only an example of a screen showing two objects compared by the comparison unit 58. The design and layout of the screen and information displayed are not limited to the contents shown in FIG. 9.

(Plan Change Unit 63)

The plan change unit 63 changes a correction plan presented by the presentation unit 54 to a seated person as needed. To describe it strictly, when a predetermined change condition is met, the plan change unit 63 changes a correction plan associated with information identifying a seated person seated in the vehicle seat S when the presentation unit 54 presents the correction plan, from the correction plan to another of the correction plans stored in the plan storage unit 53.

More specifically, in the present embodiment, posture correction is performed repeatedly for a plurality of days. In other words, each time the date when a seated person is seated in the vehicle seat S changes, correction processing is executed repeatedly on the same seated person. The measurement of a seated condition by the measurement unit 52 is also performed each time the date changes. That is, the measurement unit 52 re-measures a seated condition (specifically, the current values of the bulging pressures of the air bags and pressures applied to the seat back S1) after the date when the first correction processing is started.

Also, each time the date when a seated person is seated in the vehicle seat S changes after the date when the first correction processing is started, the plan change unit 63 determines the necessity or unnecessity of a plan change based on a seated condition re-measured by the measurement unit 52 (that is, the present measurement values). More specifically, when the comparison unit 58 compares the present measurement values with the first measurement values, the plan change unit 63 is notified of the comparison results (e.g. differences in the measurement values). The plan change unit 63 determines whether the notified comparison results satisfy the predetermined condition. When the above condition is met, the plan change unit 63 changes the correction plan. Specifically, the plan change unit 63 updates the plan management table T so as to change a correction plan associated with information identifying a seated person as a target (technically, a seated person at the point in time when a correction plan applied in the first correction processing is presented by the presentation unit 54).

As above, in the present embodiment, after a correction plan to be applied in correction processing has been determined, the correction plan is reviewed as needed. This allows a correction plan set once to be reviewed appropriately as needed according to the degree of correction of a seated posture (degree of improvement). This enables effective correction of a seated posture.

For the change of a correction plan, there are no particular limitations on which plan among correction plans stored in the plan storage unit 53 to use as a correction plan after a change. It is desirable to select an optimal plan, considering comparison results when the comparison unit 58 compares present measurement values with first measurement values. (Information Transfer Unit 61 and Information Read Unit 62)

The information transfer unit 61 transfers various kinds of information stored in the ECU 41 to the portable memory 45 connected to the ECU 41. The information read unit 62 reads information from the portable memory 45 connected to the ECU 41. That is, in the present embodiment, by using the portable memory 45, information stored in the ECU 41 can be transferred.

Here, information transferred to the portable memory 45 and read from the portable memory 45 includes measurement values when the measurement unit 52 measures a seated condition (technically, a measurement history containing past measurement values), information identifying a seated person acquired by the identification information acquisition unit 51, the correspondence relationship of a correction plan presented by the presentation unit 54 (specifically the plan management table T), a total sitting time managed by the total sitting time management unit 56, and a correction plan after a change when a correction plan is reviewed by the plan change unit 63.

In the present embodiment, the provision of the information transfer unit 61 and the information read unit 62 allows ECUs 41 mounted in different vehicles to perform transfer (handing over) of information between the ECUs 41 if each has a set of functions relating to posture correction (that is, the above-described functional units). Thus, when a vehicle to be used is changed, for example, information about posture correction stored in an ECU 41 mounted in a vehicle that has been used till then can be handed over to an ECU 41 in a vehicle newly used. As a result, a vehicle user (that is, a seated person) can continuously undergo posture correction in the new vehicle with the same correction contents as those of posture correction that he or she has undergone in the vehicle that has been used till then (that is, posture correction performed on the same correction plan).

In the present embodiment, the portable memory 45 such as a USB memory is used as an object to which the information transfer unit 61 transfers information and from which the information read unit 62 reads information, but not limited thereto. Specifically, as a substitute for the portable memory 45, a smartphone 44 held by a seated person may be used. Alternatively, the in-vehicle tablet terminal 46 may be used if the in-vehicle tablet terminal 46 is configured to be portable.

<<Operation Example of Condition Correction Unit>>

Next, as an operation example of the condition correction unit 1, a flow of posture correction by the condition correction unit 1 (posture correction flow) will be described. The posture correction flow is divided mainly into a flow when a seated person undergoes posture correction for the first time (hereinafter, a first-time flow), and a flow after the first time (hereinafter, a normal-time flow). Hereinafter, first, the first-time flow will be described, and then the normal-time flow will be described.

(First-Time Flow)

Figure 10:
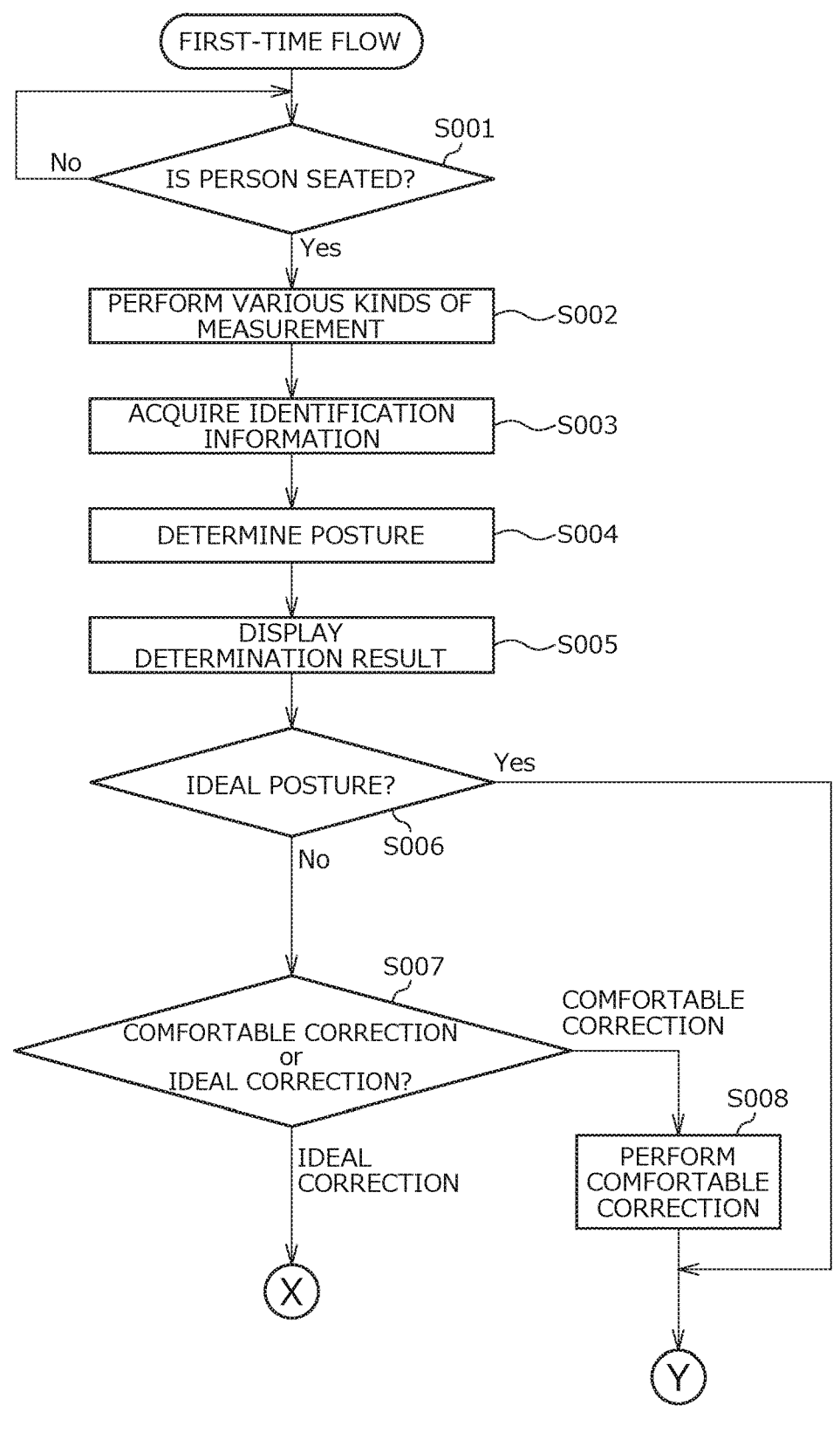
FIG. 10 is a diagram showing the flow of a first-time flow of posture correction (first).
Figure 11:
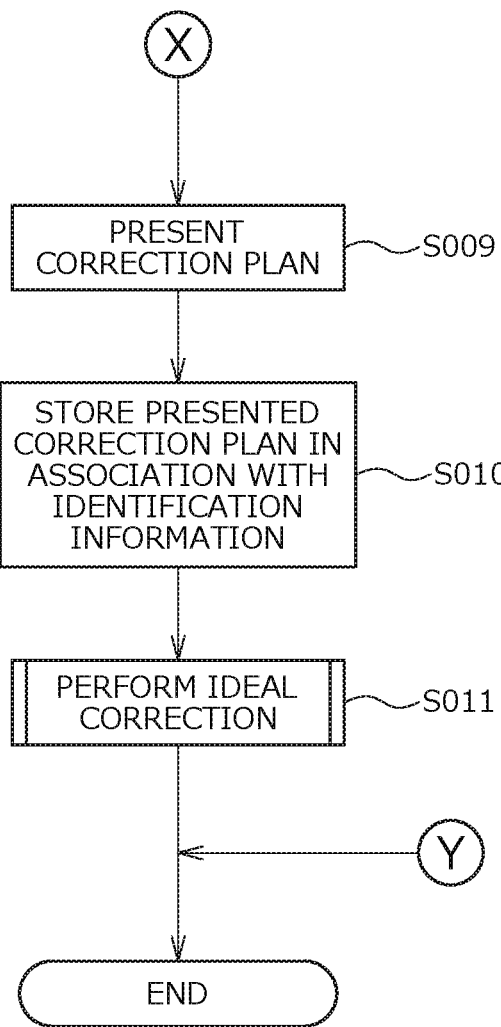
FIG. 11 is a diagram showing the flow of the first-time flow of posture correction (second).

The first-time flow proceeds according to a flow shown in FIGS. 10 and 11. Specifically, when a seated person is seated in the vehicle seat S according to the present embodiment for the first time, the first-time flow is automatically started (S001). More specifically, when a seated person is seated in the vehicle seat S, the weight sensor 34 outputs a signal corresponding to the magnitude of the seat weight changed correspondingly. The ECU 41 receives the output signal from the weight sensor 34, and with this as a trigger, automatically starts a main process of the first-time flow (process after step S002). In the present embodiment, the first-time flow is automatically started at the point in time when a seated person is seated in the vehicle seat S, but not limited thereto. A seated person may perform a predetermined operation/action after sitting down in the seat, and with the operation/action as a trigger, the first-time flow may be started.

When the first-time flow is started, the ECU 41 (specifically, the measurement unit 52) performs various kinds of measurement including measurement on the seated condition of the seated person (S002). Specifically, the bulging pressures of the air bags are measured by the bulging pressure sensors 32, and pressures applied to the portions of the seat back S1 are measured by the pressure sensors 33. In addition, sitting pressure changing with respiration is measured by the respiration sensor 31. To measure the bulging pressures of the air bags, the ECU 41 controls the actuator 18 and the electromagnetic valves V in a stage before the seated person is seated in the vehicle seat S and allows the air bags to be bulged to a predetermined bulging pressure.

Thereafter, the ECU 41 (specifically, the identification information acquisition unit 51) communicates with a smartphone 44 held by the seated person to acquire information identifying the seated person from the smartphone 44 (S003). The ECU 41 (specifically, the determination unit 60) determines the seated posture of the seated person from the seated condition measured in step S002 (S004). More specifically, the ECU 41 determines, on the basis of the current values of the bulging pressures of the air bags and the current values of the pressures applied to the portions of the seat back S1, that the current seated posture of the seated person corresponds to any of the following states: the "round-shouldered," "slightly round-shouldered," "ideal posture," "slightly backward-bent," and "backward-bent".

Then, the ECU 41 (specifically, the information display unit 59) generates information display data for displaying the determined seated posture and transmits it to the in-vehicle tablet terminal 46. Consequently, a seated posture determination result is displayed on the touch panel 46a of the in-vehicle tablet terminal 46 (S005).

Thereafter, the ECU 41 performs the following process according to the seated posture determination result. Specifically, when the determined seated posture is the ideal posture (Yes in S006), the ECU 41 terminates the first-time flow. Meanwhile, when the determined seated posture is a posture other than the ideal posture (No in S006), the ECU 41 performs the following process with a mode designation operation by the seated person as a trigger.

Here, to describe the mode designation operation by the seated person, the mode designation operation is an operation performed to designate one of a plurality of candidates prepared for control modes of the ECU 41. In the present embodiment, the operation is performed through the touch panel 46*a* of the in-vehicle tablet terminal 46. Two candidates are prepared as control modes by the ECU 41. Specifically, a "comfortable correction" mode and an "ideal correction" mode are set. The "ideal correction" mode is a mode to perform posture correction, and specifically, is a mode to control the actuator 18, the electromagnetic valves V, and others so that the current seated posture is corrected to the ideal posture.

The "comfortable correction" mode is a mode to stabilize the current seated posture as it is, and is a mode to control the actuator 18, the electromagnetic valves V, and others so that the seated person can easily keep the current seated posture.

In order to designate one of the above two control modes, the seated person presses one of two designation buttons (buttons with letters "comfortable correction" and "ideal correction" in FIG. 7) displayed on the touch panel 46*a* together with the seated posture determination result. This button operation is the mode designation operation. The ECU 41 receives the operation through the in-vehicle tablet terminal 46.

When the "comfortable correction" mode is designated ("comfortable correction" in S007), the ECU 41 performs the above-described comfortable correction (S008).

Meanwhile, when the "ideal correction" mode is designated ("ideal correction" in S007), the ECU 41 performs the above-described ideal correction. To perform the ideal correction, the ECU 41 (specifically, the presentation unit 54) accesses the plan storage unit 53, and reads a correction plan suitable for the current seated posture of the seated person determined in the previous step S004 from the correction plans stored in the plan storage unit 53. Then, the ECU 41 presents the read correction plan to the seated person (S009). More specifically, the ECU 41 (specifically, the information display unit 59) generates information display data for displaying the read correction plan and transmits it to the in-vehicle tablet terminal 46. Consequently, as shown in FIG. 8, the correction plan read by the ECU 41, that is, the correction plan suitable for the current seated posture of the seated person is displayed (presented) on the touch panel 46*a* of the in-vehicle tablet terminal 46.

The ECU 41 stores the presented correction plan in association with the information identifying the seated person acquired in the previous step S003 in the plan storage unit 53 (S010). Specifically, the ECU 41 updates the plan management table T so that a record in which the identification information and the correction plan are associated with each other is added into the plan management table T.

Thereafter, when the seated person gives a command to perform ideal correction with the in-vehicle tablet terminal 46 (specifically, presses a button with the letters "start correction" in FIG. 8), with this as a trigger, the ECU 41 performs ideal correction (S011). The ideal correction proceeds by the ECU 41 executing steps shown in FIG. 12.

Specifically, in the ideal correction, the ECU 41 (specifically, the processing execution unit 55) reads the correction plan associated with the information identifying the seated person seated in the vehicle seat S from the plan storage unit 53 (S021).

Next, the ECU 41 (specifically, the processing execution unit 55) controls the heater 15 to warm the predetermined part of the back of the seated person (S022), and controls the vibration application device 16 to apply vibrations to the back of the seated person (S023). Therefore, muscles (especially muscles of the shoulders, back, and waist) of the seated person are relaxed, and then the subsequent posture correction is efficiently performed.

Figure 13:
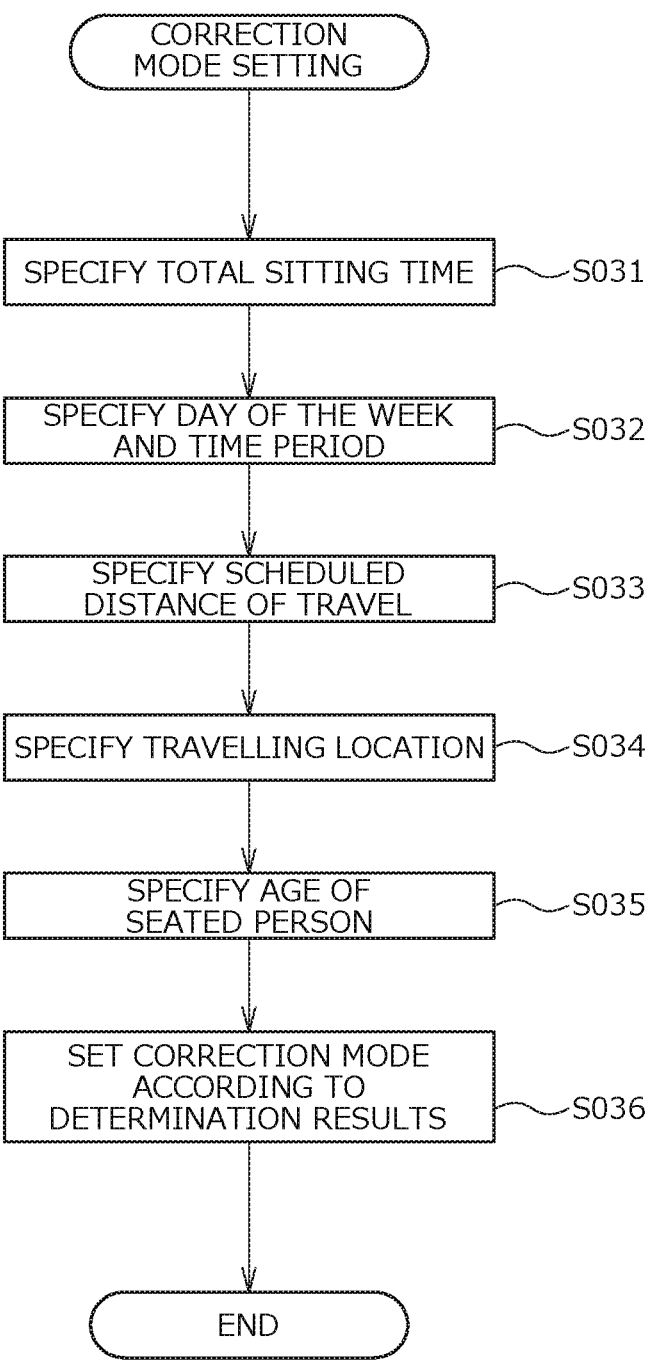
FIG. 13 is a diagram showing a process of correction mode setting.

Thereafter, the ECU 41 (specifically, the mode setting unit 57) sets a correction mode to be applied during correction processing (S024). To describe a process to set a correction mode, as shown in FIG. 13, the ECU 41 (specifically, the total sitting time management unit 56) determines the total sitting time of the seated person seated in the vehicle seat S at that point in time (S031). In a stage immediately after the start of the first-time flow, the total sitting time is zero.

Thereafter, the ECU 41 (specifically, the mode setting unit 57) determines the day of the week of that day and the current time period (S032). The ECU 41 (specifically, the mode setting unit 57) communicates with the car navigation device 43 to determine the scheduled distance of travel of the vehicle on that day (S033). The ECU 41 (specifically, the mode setting unit 57) determines the current traveling place of the vehicle, more specifically, whether the vehicle is travelling on an expressway, on the basis of a signal received from an ETC 47 or the like (S034). Further, the ECU 41 (specifically, the mode setting unit 57) specifies the age of the seated person entered by the seated person through the in-vehicle tablet terminal 46 (S035). After completing such a series of determination steps, the ECU 41 (specifically, the mode setting unit 57) sets a correction mode according to the determination results in the previous steps S031 to S035 (S036).

After setting the correction mode, the ECU 41 (specifically, the processing execution unit 55) executes correction processing in the correction mode set in the previous step S036, according to correction contents shown by the correction plan read in the previous step S021 (S025).

Figure 12:
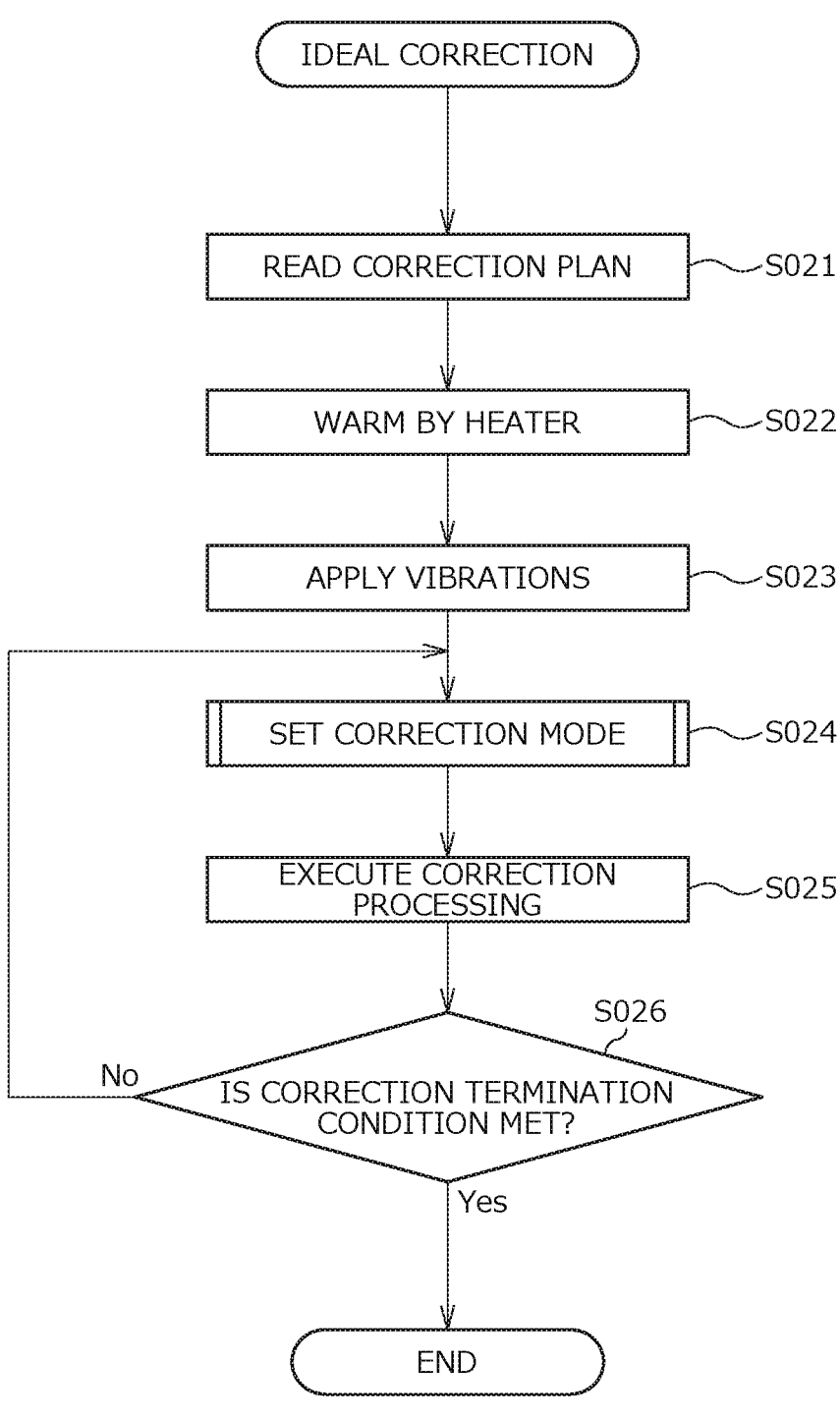
FIG. 12 is a diagram showing a process of ideal correction of posture.

Then, as shown in FIG. 12, the ECU 41 (specifically, the processing execution unit 55) periodically repeats the step of setting a correction mode and the step of executing correction processing until a correction termination condition is met (S026). The correction termination condition defines the timing to terminate execution of ideal correction of that day (one day). Examples of the correction termination condition include a lapse of a pre-specified correction time, an arrival of the vehicle at a destination, and an operation being performed by the seated person to give an instruction for correction termination.

At the point in time when the correction termination condition is met, the posture correction for the first time is completed, and the first-time flow ends.

(Normal-Time Flow)

Figure 14:
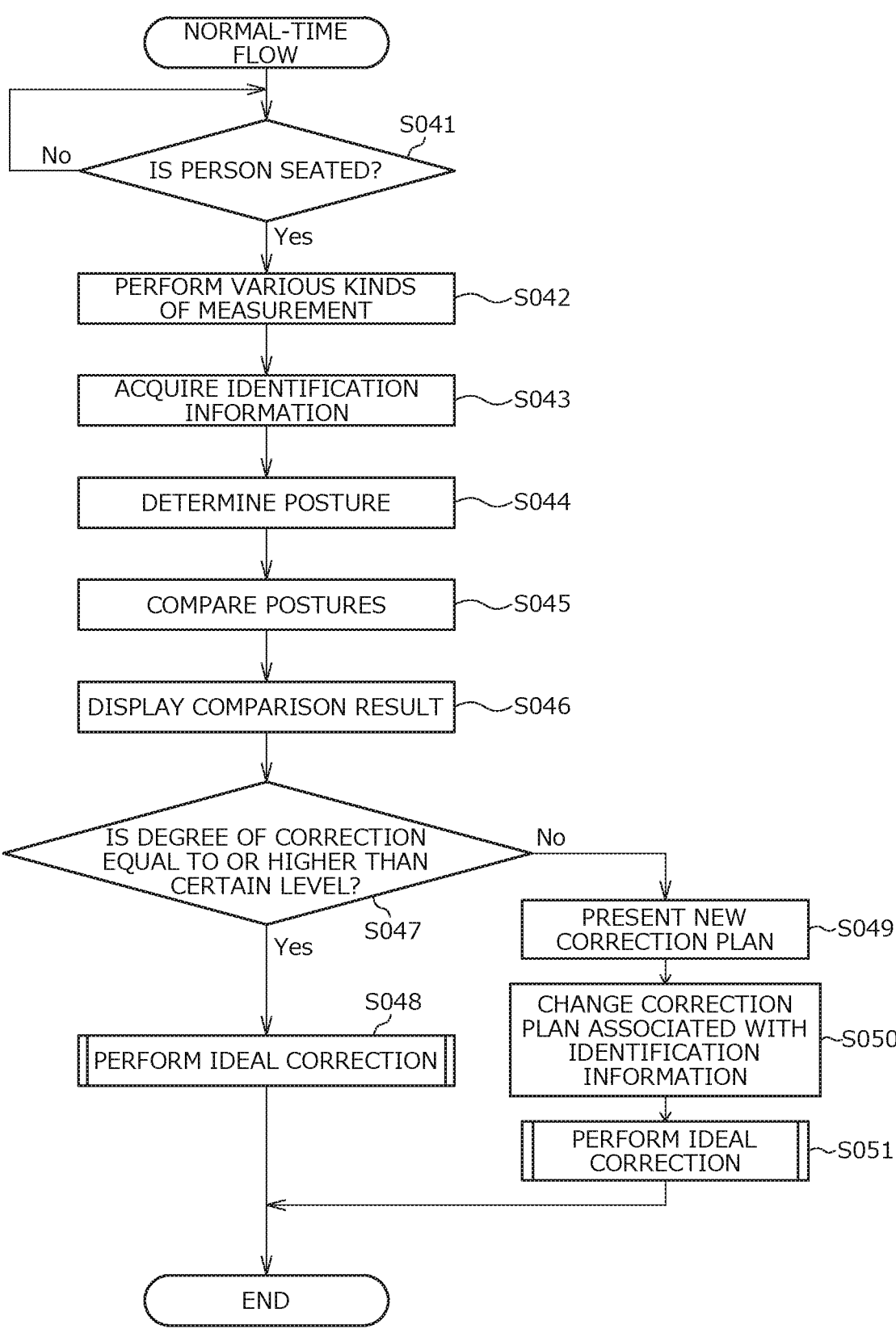
FIG. 14 is a diagram showing the flow of a normal-time flow of posture correction.

The normal-time flow is performed after a day when the first-time flow is performed, and proceeds according to a flow shown in FIG. 14. Specifically, like the first-time flow, the normal-time flow is automatically started at the point in time when a seated person is seated in the vehicle seat S (S041). Thereafter, the ECU 41 performs various kinds of measurement on the seated condition or the like of the seated person (S042), acquisition of information identifying the seated person (S043), and determination of the seated posture (S044) by a process similar to that in the first-time flow.

As described above, in the present embodiment, the ECU 41 performs the measurement of a seated condition, the acquisition of identification information, and the determination of a seated posture, as a routine common to the first-time flow and the normal-time flow. When the acquired identification information is coincided with identification information acquired previously, the ECU 41 subsequently performs the normal-time flow by the process shown in FIG. 14. The fact that the normal-time flow is performed means that for a seated person having the same identification information, the measurement of a seated condition and the determination of a seated posture are performed over a period of multiple days. In other words, in the normal-time flow, the seated posture of a seated person is re-measured after the day when the first-time flow is performed.

After the determination of the seated posture in the normal-time flow, the ECU 41 (specifically, the comparison unit 58) performs posture comparison (S045). Specifically, in the posture comparison, the measurement values of the seated condition in the first-time flow (the first measurement values) are compared with the measurement values of the seated condition measured this time in the normal-time flow (the present measurement values).

Thereafter, the ECU 41 (specifically the information display unit 59) generates information display data for displaying the results of the posture comparison and transmits it to the in-vehicle tablet terminal 46. Consequently, as shown in FIG. 9, the comparison results of the seated postures, specifically pieces of image information based on the present measurement values and the first measurement values, respectively, are displayed on the touch panel 46a of the in-vehicle tablet terminal 46 (S046). Thus, the seated person grasps the effect of the posture correction (the degree of posture improvement) that has been performed until the last time through the touch panel 46a.

Meanwhile, the ECU 41 (specifically the plan change unit 63) determines on the basis of the comparison results in the previous step S046 whether to change the correction plan to be applied at the time of correcting the posture of the seated person (technically, the seated person seated in the vehicle seat S at the time). Specifically, the ECU 41 specifies the degree of correction on the seated posture of the seated person from the comparison results, and when the correction degree is equal to or higher than a certain level (Yes in S047), the plan is not changed. In this case, in a situation where ideal correction (that is, posture correction) is performed on the seated person having the same identification information, the ECU 41 continues to apply the correction plan that has been associated with the identification information up to that time, therefore performing ideal correction (S048).

By contrast, when the correction degree is less than the certain level (No in S047), the ECU 41 (specifically, the presentation unit 54) reads a correction plan suitable for the correction degree at that point in time from the correction plans stored in the plan storage unit 53, and presents the correction plan as a new correction plan to the seated person (S049). Then, the ECU 41 (specifically the plan change unit 63) changes the correction plan associated with the information identifying the seated person to which the new correction plan is presented (S050). Specifically, the ECU 41 updates the plan management table T so that the above plan change is reflected. After that, the ECU 41 (specifically, the processing execution unit 55) performs ideal correction (that is, posture correction) on the changed correction plan (S051).

In the normal-time flow, ideal correction proceeds in a process similar to that in the first-time flow (that is, the process shown in FIG. 12). Also, in the normal-time flow, the step of setting a correction mode and the step of executing correction processing are repeated periodically until the correction termination condition is met. At the point in time when the correction termination condition is met, the posture correction of that day is completed, and the normal-time flow ends.

Other Embodiments

Although the condition correction unit of the present disclosure has been mainly described in the above embodiment, the above embodiment is intended to facilitate understanding of the present disclosure and is not intended to limit the present disclosure. That is, it will be understood that the present disclosure can be altered and modified without departing from its scope and that the present disclosure includes its equivalents.

In the above embodiment, a plurality of correction plans has been prepared in a stage before a seated person is seated in the vehicle seat S, and has been stored in the plan storage unit 53 in advance, but not limited thereto. After a seated person has sat down in the vehicle seat S, for example, after the seated condition of the seated person has been measured, a correction plan reflective of the measurement values may be newly created.

In the above embodiment, a case where posture correction is repeatedly performed on the same seated person over a period of multiple days has been described as an example, but not limited thereto. The present disclosure is also applicable to a case where posture correction is performed on a seated person at one time.

In the above embodiment, the condition correction unit 1 of the present disclosure is used mainly for the purpose of correcting the seated posture of a seated person. However, the use of the condition correction unit 1 is not particularly limited, and the condition correction unit 1 may be used for correcting body condition other than seated posture, such as muscle strength, flexibility, and skeletal distortion.

REFERENCE SIGNS LIST

1: condition correction unit
11: shoulder support
    11a: shoulder air bag (operating unit, air bag)
12: lumbar support
    12a: lumbar air bag (operating unit, air bag)
13: pelvis support
    13a: pelvis air bag (operating unit, air bag)
14: side support
15: heater (warming unit)
16: vibration application device (vibration application unit)
18: actuator (operating unit)
31: respiration sensor
32: bulging pressure sensor
33: pressure sensor
34: weight sensor
41: ECU
42: vehicle speed sensor
43: car navigation device
44: smartphone (portable terminal)
45: portable memory
46: in-vehicle tablet terminal
    46a: touch panel
47: ETC
51: identification information acquisition unit
52: measurement unit
53: plan storage unit
54: presentation unit
55: processing execution unit
56: total sitting time management unit
57: mode setting unit
58: comparison unit
59: information display unit
60: determination unit
61: information transfer unit
62: information read unit
63: plan change unit S: vehicle seat S1: seat back S2: seat cushion S3: headrest

FPTS-PCT352-US-DI

T: plan management table

What is claimed is:

1. A condition correction unit comprising:

an operator configured to operate to correct a body condition of a seated person seated in a seat;

a control circuit configured to measure a current value of an indicator for determining the body condition and to execute processing to correct the body condition by controlling the operator;

a memory configured to store correction plans showing contents of correction of the body condition;

a heater configured to warm a predetermined part of the body of the seated person seated in the seat;

a bulging pressure sensor configured to measure a bulging pressure of an air bag disposed in a seat back of the seat; and a pressure sensor provided on the air bag and configured to measure a pressure applied to the seat back, wherein controlling modes to be performed by the control circuit include:

an ideal correction mode that is a mode to control the operator to correct a seated posture of the seated person to an ideal posture, wherein the ideal posture is a preselected posture as an ultimate goal for the seated person; and a comfortable correction mode that is a mode to control the operator to allow the seated person to keep a current seated posture for stabilizing the current seated posture of the seated person as it is, wherein one of the controlling modes is designatable, wherein the indicator includes the bulging pressure of the air bag measured by the bulging pressure sensor and pressure applied to the seat back measured by the pressure sensor, wherein the control circuit determines the current seated posture of the seated person based on the measured current value of the bulging pressure of the air bag and the measured current value of the pressure applied to the seat back, wherein, when a determination result of the current seated posture of the seated person determined based on the measured current value of the bulging pressure of the air bag and the measured current value of the pressure applied to the seat back is not the ideal posture, the control circuit allows designation of one of the ideal correction mode and the comfortable correction mode by the seated person, wherein the control circuit receives designation of the one of the controlling modes after measuring the current value of the indicator, wherein the control circuit executes the processing to correct the body condition according to the contents of the correction shown by the correction plans read from the memory suitable for the current seated posture of the seated person and adjusts the bulging pressure of the air bag in accordance with the determination result of the current seated posture of the seated person, and wherein, upon receipt of a signal indicating that the seated person is seated in the seat or upon a predetermined operation performed after the seated person is seated in the seat, and in response to the designation of the ideal correction mode, the control circuit controls the heater to warm the predetermined part of the body of the seated person before the control circuit executes the processing to correct the body condition.

2. The condition correction unit according to claim 1, further comprising a vibrator configured to apply vibrations to the predetermined part of the body of the seated person seated in the seat, wherein the control circuit controls the heater to warm the predetermined part of the body of the seated person before the control circuit controls the vibrator to apply a vibration to the predetermined part of the body of the seated person.

3. The condition correction unit according to claim 2, wherein the heater is disposed below the vibrator in the seat.

4. The condition correction unit according to claim 2, wherein the heater and the vibrator are provided in a seat back of the seat, and wherein the heater is disposed below the vibrator in the seat.

5. The condition correction unit according to claim 2, wherein the heater is disposed above the vibrator in the seat.

6. The condition correction unit according to claim 2, wherein the heater and the vibrator are provided in a seat back of the seat, and wherein the heater is disposed above the vibrator in the seat.

7. The condition correction unit according to claim 1, wherein the operator includes a plurality of operators, and wherein the heater is disposed between the plurality of operators in the seat.

8. The condition correction unit according to claim 1, further comprising:

an information display unit configured to transmit information to a terminal having a monitor screen and display the information on the monitor screen, wherein the information display unit transmits information based on two measurement values to be compared as information on a degree of posture improvement to the terminal and display the information on the monitor screen.

9. The condition correction unit according to claim 1, further comprising:

a weight sensor for measuring a seated condition of the seated person, wherein the heater is disposed above and at a rear of the weight sensor in the seat.

10. The condition correction unit according to claim 1, wherein the operator includes the air bag, wherein the air bag is bulged to a preset bulging pressure in a stage before the seated person is seated in the seat, wherein the control circuit measures, through the bulging pressure sensor, the current value of the bulging pressure of the air bag changed when the seated person is seated in the seat as the current value of the indicator, and determines the current seated posture of the seated person based on the measured changed current value of the bulging pressure of the air bag.

11. A method for correcting a body condition of a seated person seated in a seat using a condition correction unit, wherein the condition correction unit comprises an operator configured to operate to correct a body condition of the seated person, a control circuit configured to measure a current value of an indicator for determining the body condition and to execute processing to correct the body condition by controlling the operator, a memory configured to store correction plans showing contents of correction of the body condition, a heater configured to warm a predetermined part of the body of the seated person, a bulging pressure sensor configured to measure a bulging pressure of an air bag disposed in a seat back of the seat, and a pressure sensor provided on the air bag and configured to measure a pressure applied to the seat back, the method comprising:

receiving, by the control circuit, one of controlling modes designated among the controlling modes, after measuring the current value of the indicator by the control circuit, wherein the controlling modes are modes to be performed by the control circuit and include an ideal correction mode that is a mode to control the operator to correct a seated posture of the seated person to an ideal posture, wherein the ideal posture is a preselected posture as an ultimate goal for the seated person, and a comfortable correction mode that is a mode to control the operator to allow the seated person to keep a current seated posture for stabilizing the current seated posture of the seated person as it is, wherein the indicator includes the bulging pressure of the air bag measured by the bulging pressure sensor and the pressure applied to the seat back measured by the pressure sensor;

determining, by the control circuit, the current seated posture of the seated person based on the measured current value of the bulging pressure of the air bag and the measured current value of the pressure applied to the seat back;

when a determination result of the current seated posture of the seated person determined based on the measured current value of the bulging pressure of the air bag and the measured current value of the pressure applied to the seat back is not the ideal posture, allowing, by the control circuit, designation of one of the ideal correction mode and the comfortable correction mode by the seated person;

reading, by the control circuit, a correction plan from the memory suitable for the current seated posture of the seated person;

executing, by the control circuit, the processing to correct the body condition according to the contents of the correction shown by the read correction plan and adjusting the bulging pressure of the air bag in accordance with the determination result of the current seated posture of the seated person; and upon receipt of a signal indicating that the seated person is seated in the seat or upon a predetermined operation performed after the seated person is seated in the seat, and in response to designation of the ideal correction mode, controlling, by the control circuit, the heater to warm the predetermined part of the body of the seated person before executing the processing to correct the body condition.

12. The method according to claim 11, wherein the condition correction unit further comprises a vibrator configured to apply vibrations to the predetermined part of the body of the seated person seated in the seat, the method further comprising:

controlling, by the control circuit, the heater to warm the predetermined part of the body of the seated person before controlling the vibrator to apply a vibration to the predetermined part of the body of the seated person.

13. The method according to claim 12, wherein the heater is disposed below the vibrator in the seat.

14. The method according to claim 12, wherein the heater and the vibrator are provided in a seat back of the seat, and wherein the heater is disposed below the vibrator in the seat.

15. The method according to claim 12, wherein the heater is disposed above the vibrator in the seat.

16. The method according to claim 12, wherein the heater and the vibrator are provided in a seat back of the seat, and wherein the heater is disposed above the vibrator in the seat.

17. The method according to claim 11, wherein the operator includes a plurality of operators, and wherein the heater is disposed between the plurality of operators in the seat.

18. The method according to claim 11, wherein the condition correction unit further comprises an information display unit configured to transmit information to a terminal having a monitor screen and display the information on the monitor screen, the method further comprising:

transmitting, by the information display unit, information based on two measurement values to be compared as information on a degree of posture improvement to the terminal, and displaying the information on the monitor screen.

19. The method according to claim 11, wherein the condition correction unit further comprises a weight sensor for measuring a seated condition of the seated person, and wherein the heater is disposed above and at a rear of the weight sensor in the seat.

20. The method according to claim 11, further comprising:

bulging the air bag to a preset bulging pressure in a stage before the seated person is seated in the seat; and measuring, by the control circuit, the current value of the bulging pressure of the air bag changed when the seated person is seated in the seat as the current value of the indicator through the bulging pressure sensor, wherein the control circuit determines the current seated posture of the seated person based on the measured changed current value of the bulging pressure of the air bag.

* * * * *